United States Patent
Del Cardayre et al.

(10) Patent No.: US 8,535,916 B2
(45) Date of Patent: Sep. 17, 2013

(54) MODIFIED MICROORGANISMS AND USES THEREFOR

(75) Inventors: Stephen B. Del Cardayre, Belmont, CA (US); Shane Brubaker, Oakland, CA (US); Jay D. Keasling, Berkeley, CA (US)

(73) Assignee: LS9, Inc., South San Francisco, CA (US)

( * ) Notice: Subject to any disclaimer, the term of this patent is extended or adjusted under 35 U.S.C. 154(b) by 497 days.

(21) Appl. No.: 12/526,209

(22) PCT Filed: Feb. 13, 2007

(86) PCT No.: PCT/US2007/003736
§ 371 (c)(1),
(2), (4) Date: Dec. 6, 2010

(87) PCT Pub. No.: WO2008/100251
PCT Pub. Date: Aug. 21, 2008

(65) Prior Publication Data
US 2011/0097769 A1     Apr. 28, 2011

(51) Int. Cl.
*C12P 7/64*     (2006.01)

(52) U.S. Cl.
USPC .......................................................... 435/134

(58) Field of Classification Search
USPC .......................................................... 435/134
See application file for complete search history.

(56) References Cited

PUBLICATIONS

IPER—PCT/US2007/003736 (2007).*
Ohmiya et al. Journal of Bioscience and Bioengineering, 95(6): 549-561 (2003).*

* cited by examiner

*Primary Examiner* — Tekchand Saidha
(74) *Attorney, Agent, or Firm* — Brigitte A. Hajos

(57) ABSTRACT

The invention provides a genetically modified microorganism that acquires the ability to consume a renewable feedstock (such as cellulose) and produce products. This organism can be used to ferment cellulose, one of the most abundant renewable resources available, and produce products.

8 Claims, 1 Drawing Sheet

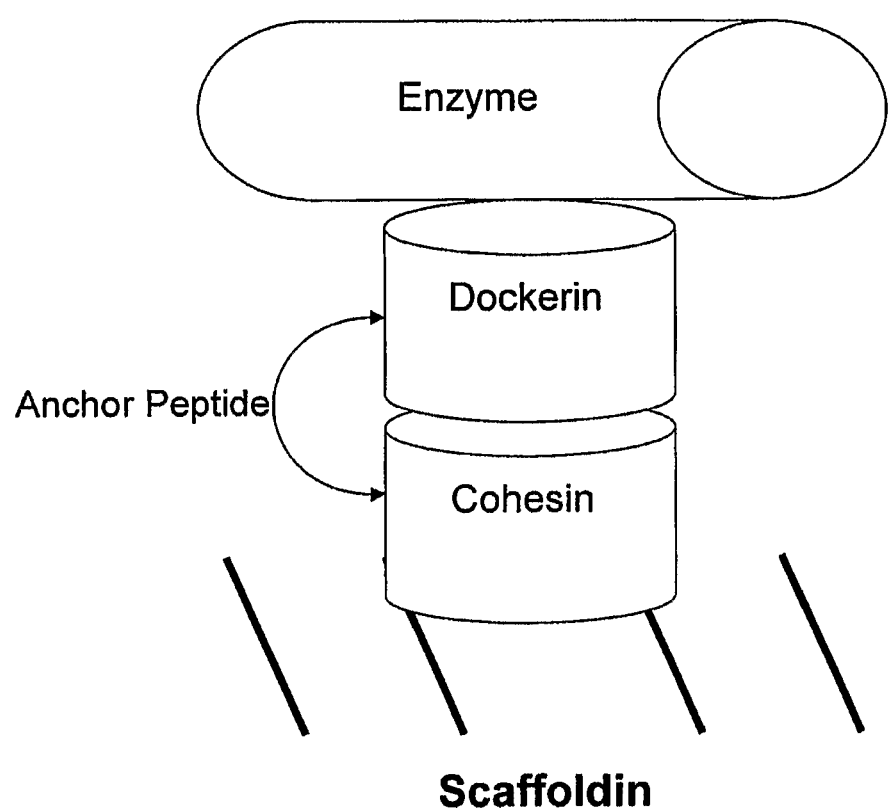

SEQUENCE LISTING

```
<160> NUMBER OF SEQ ID NOS: 4

<210> SEQ ID NO 1
<211> LENGTH: 71
<212> TYPE: PRT
<213> ORGANISM: Clostridium cellulovorans
<220> FEATURE:
<221> NAME/KEY: MOD_RES
<222> LOCATION: (1)..(1)
<223> OTHER INFORMATION: Any naturally occurring amino acid

<400> SEQUENCE: 1

Xaa Ser Thr Lys Leu Tyr Gly Asp Val Asn Asp Asp Gly Lys Val Asn
1               5                   10                  15

Ser Thr Asp Ala Val Ala Leu Lys Arg Tyr Val Leu Arg Ser Gly Ile
            20                  25                  30

Ser Ile Asn Thr Asp Asn Ala Asp Leu Asn Glu Asp Gly Arg Val Asn
        35                  40                  45

Ser Thr Asp Leu Gly Ile Leu Lys Arg Tyr Ile Leu Lys Glu Ile Asp
    50                  55                  60

Thr Leu Pro Tyr Lys Asn Gly
65                  70

<210> SEQ ID NO 2
<211> LENGTH: 216
<212> TYPE: PRT
<213> ORGANISM: Clostridium cellulovorans

<400> SEQUENCE: 2

Glu Phe Asn Phe Asn Tyr Trp Lys Thr Gln Val Thr Thr Thr Pro Gly
1               5                   10                  15

Gly Leu Lys Trp Leu Ser Asn Trp Gly Val Leu Arg Tyr Ala Ala Ala
            20                  25                  30

Glu Ser Met Val Met Leu Val Tyr Cys Lys Gln Asn Pro Asp Gln Ser
        35                  40                  45

Leu Leu Asp Leu Ala Lys Lys Gln Val Asp Tyr Ile Leu Gly Asp Asn
    50                  55                  60

Pro Ala Asn Met Ser Tyr Ile Ile Gly Tyr Gly Ser Asn Trp Cys Ile
65                  70                  75                  80

His Pro His His Arg Ala Ala Asn Gly Tyr Thr Tyr Ala Asn Gly Asp
                85                  90                  95

Asn Ala Lys Pro Ala Lys His Leu Leu Thr Gly Ala Leu Val Gly Gly
            100                 105                 110

Pro Asp Gln Asn Asp Lys Phe Leu Asp Asp Ala Asn Gln Tyr Gln Tyr
        115                 120                 125

Thr Glu Val Ala Leu Asp Tyr Asn Ala Gly Leu Val Gly Val Leu Ala
```

```
            130                 135                 140
Gly Ala Ile Lys Phe Phe Gly Gly Thr Ile Val Asn Pro Pro Val Lys
145                 150                 155                 160

Lys Gly Asp Leu Asn Asn Asp Thr Phe Ile Asp Ala Ile Asp Leu Ala
                165                 170                 175

Leu Cys Lys Asn Tyr Ile Leu Thr Gln Asn Gly Asn Ile Asp Lys Asn
                180                 185                 190

Asn Ala Asp Met Asn Gly Asp Gly Ser Ile Asp Ala Ile Asp Phe Ser
                195                 200                 205

Leu Leu Lys Lys Ala Ile Leu Gly
    210                 215

<210> SEQ ID NO 3
<211> LENGTH: 145
<212> TYPE: PRT
<213> ORGANISM: Clostridium cellulovorans

<400> SEQUENCE: 3

Lys Asp Ile Pro Gly Asp Ser Leu Lys Val Thr Val Gly Thr Ala Asn
1               5                   10                  15

Gly Lys Pro Gly Asp Thr Val Thr Val Pro Val Thr Phe Ala Asp Val
                20                  25                  30

Ala Lys Met Lys Asn Val Gly Thr Cys Asn Phe Tyr Leu Gly Tyr Asp
            35                  40                  45

Ala Ser Leu Leu Glu Val Val Ser Val Asp Ala Gly Pro Ile Val Lys
        50                  55                  60

Asn Ala Val Asn Phe Ser Ser Ser Ala Ser Asn Gly Thr Ile Ser
65                  70                  75                  80

Phe Leu Phe Leu Asp Asn Thr Ile Thr Asp Glu Leu Ile Thr Ala Asp
                85                  90                  95

Gly Val Phe Ala Asn Ile Lys Phe Lys Leu Lys Ser Val Thr Ala Lys
            100                 105                 110

Thr Thr Thr Pro Val Thr Phe Lys Asp Gly Gly Ala Phe Gly Asp Gly
        115                 120                 125

Thr Met Ser Lys Ile Ala Ser Val Thr Lys Thr Asn Gly Ser Val Thr
    130                 135                 140

Ile
145

<210> SEQ ID NO 4
<211> LENGTH: 138
<212> TYPE: PRT
<213> ORGANISM: Clostridium cellulovorans

<400> SEQUENCE: 4

Met Thr Val Glu Ile Gly Lys Val Thr Ala Ala Val Gly Ser Lys Val
1               5                   10                  15

Glu Ile Pro Ile Thr Leu Lys Gly Val Pro Ser Lys Gly Met Ala Asn
                20                  25                  30

Cys Asp Phe Val Leu Gly Tyr Asp Pro Asn Val Leu Glu Val Thr Glu
            35                  40                  45

Val Lys Pro Gly Ser Ile Ile Lys Asp Pro Asp Pro Ser Lys Ser Phe
        50                  55                  60

Asp Ser Ala Ile Tyr Pro Asp Arg Lys Met Ile Val Phe Leu Phe Ala
65                  70                  75                  80

Glu Asp Ser Gly Arg Gly Thr Tyr Ala Ile Thr Gln Asp Gly Val Phe
                85                  90                  95
```

-continued

```
Ala Thr Ile Val Ala Thr Val Lys Ser Ala Ala Ala Ala Pro Ile Thr
            100                 105                 110

Leu Leu Glu Val Gly Ala Phe Ala Asp Asn Asp Leu Val Glu Ile Ser
        115                 120                 125

Thr Thr Phe Val Ala Gly Gly Val Asn Leu
        130                 135
```

MODIFIED MICROORGANISMS AND USES THEREFOR

CROSS REFERENCE TO RELATED APPLICATIONS

This application claims the benefit of the earlier filing date of U.S. provisional application No. 60/772,682, filed Feb. 13, 2006, which is incorporated herein by reference.

FIELD

Disclosed are microorganisms that have been engineered to degrade cellulosic material to make products and embodiments of a method for making products therefrom.

SEQUENCE LISTING

The instant application contains a Sequence Listing which has been submitted in ASCII format via EFS-Web and is hereby incorporated by reference in its entirety. Said ASCII copy, created on Jun. 14, 2013, is named LS00001PCT-US_SL.txt and is 5,620 bytes in size.

BACKGROUND OF THE INVENTION

For centuries, humans have been domesticating and breeding organisms to solve human problems and to improve their quality of life. Since the advent of molecular biology, genetic engineering has become the preferred route to improve microbial traits. In contrast to breeding, genetic engineering has focused largely on isolated pathways or regulatory circuits without considering the organism as a whole. Not surprisingly, the genetic redirection often falls short in meeting its full potential when the manipulated pathway is considered in vacuuo.

Many microorganisms have unique abilities to utilize renewable energy sources, such as cellulose, one of the most abundant renewable resources available. Other microorganisms are able to synthesize useful products, such as various hydrocarbons using simple sugar sources, such as those resulting from cellulose digestion. Unfortunately, the genetics and biochemistry of such microorganisms are not as well-known as compared to other genetically tractable model microbes, such as E. coli or Bacillus subtilis. In addition, the cultivation conditions for such microorganisms are frequently difficult or uneconomical to provide, thus hindering the use of these potentially useful microorganisms.

Thus there is a need to engineer microorganisms that make useful products from inexpensive renewable carbon sources. This requires the combination of traits from different organisms into one organism that can be industrially exploited.

SUMMARY

One aspect of the invention provides a method for modifying a microorganism to produce hydrocarbons from a renewable energy source, such as cellulosic material, comprising: (1) obtaining, from a first heterologous organism, first genes encoding proteins, such as proteins that encode synthetic cellulosomes, that transform the renewable energy source, such as cellulosic material, to a carbon source; (2) obtaining, from (a) second heterologous organism(s), second gene(s) for biosynthesis of products, such as hydrocarbons from the carbon source; (3) introducing the first genes and the second gene(s) into the microorganism, such that the first genes and the second gene(s) are functionally expressed to confer to the microorganism the ability to transform the renewable energy source to provide the carbon source for production of the hydrocarbon; wherein steps (1) and (2) are performed in any order before step (3).

In one embodiment, the method further comprises: (4) eliminating undesirable side reactions that tend to consume substrate and/or energy without producing the hydrocarbons, in order to improve production yields of the hydrocarbons.

In one embodiment, the microorganism is genetically tractable and/or cultivable.

In one embodiment, the hydrocarbons comprise any hydrocarbon suitable for biofuel, such as, saturated hydrocarbons or alkanes, or unsaturated hydrocarbons selected from: alkenes, alkynes, or dienes, or a combination thereof.

In one embodiment, the first genes comprise one or more of: cellulase, cellobiohydrolase, xylanase, amylase, lignin peroxidase (LiP); manganese peroxidase (MnP); laccase (Lac); glyoxal oxidase (GLOX); flavin adenine dinucleotide enzymes such as pyranose 2-oxidase, aryl alcohol oxidase, cellobiose dehydrogenase (CDH); auxiliary enzymes such as methanol oxidase, 1,4-benzoquinone reductase, methyltransferases, cytochrome P450, L-phenylalanine ammonialyase, 1,2,4-trihydroxybenzene 1,2-dioxygenase, glutathione transferases, superoxide dismutase, catalase or combinations thereof.

In one embodiment, the first genes encoding cellulosome proteins are obtained by sequence homology searching in the genome of the first heterologous organisms, using a query sequence from a known cellulosome gene.

In one embodiment, the first genes encoding cellulosome proteins are obtained by functional screening of the first heterologous organism, using DNA from the first heterologous organism.

In one embodiment, at least one of the first genes and/or the second genes are at least partially under the control of an inducible promoter or a constitutive promoter.

In one embodiment, at least one of the first genes and/or the second genes are integrated into the genome of the microorganism or are in an extrachromosomal genetic element.

In one embodiment, the first genes and/or the second genes are introduced into the microorganism by a viral vector, a phage, a plasmid, a phagemid, a cosmid, a phosmid, a bacterial artificial chromosome (BAC), a bacteriophage P1, a P1-based artificial chromosome (PAC), a yeast artificial chromosome (YAC), or a yeast plasmid.

Also, described herein are isolated microorganisms that contain one or more exogenous nucleic acid sequences. These nucleic acid sequences encode at least one product-forming peptide which enables the microorganism to produce products that are useful as biofuels, nutritional supplements, and as replacements for products that are derived from petroleum. The exogenous nucleic acid sequences also encode synthetic cellulosomes which function to allow the microorganism to utilize cellulosic material as a source of carbon.

In some examples the synthetic cellulosome contains a structural peptide sequence. Any structural peptide sequence known in the art can be used. In some instances the structural peptide has an amino acid sequence having at least, 65%, 70%, 75%, 80%, 85%, 90%, or 95% sequence identity to a carbohydrate binding module (CBM, Accessions: ZP_00510056), SLH module (Accessions: ZP_005100961), Scaffoldin (Accesssions: AY221113) or combinations thereof.

In other examples the synthetic cellulosome contains a dockerin domain sequence. Any dockerin domain sequence known in the art can be used. In some instances a dockerin domain sequence having at least 65%, 70%, 75%, 80%, 85%, 90%, 95% sequence identity to SEQ ID NOS: 1-2 or combinations thereof, is used.

In other examples the synthetic cellulosome contains a cohesin domain sequence. Any cohesin domain sequence known in the art can be used. In some instances a cohesin domain sequence having at least 65%, 70%, 75%, 80%, 85%, 90%, 95% sequence identity to SEQ ID NOS: 3-4 or combinations thereof, is used.

One of ordinary skill in the art will appreciate that any product that has been made using engineered microorganisms can be made utilizing the production hosts (microorganisms described herein expressing synthetic cellulosomes and product-forming enzymes/peptides). One of ordinary skill in the art will also appreciate that the choice of product-forming peptide expressed will depend upon what the desired product is. Exemplary, product-forming peptides (in most instances having enzymatic activity) include, without limitation geranyl pyrophosphate synthase (EC 2.5.1.1), geranylgeranyl pyrophosphate synthase (Accessions: XM_001275554, EC 2.5.1.-), phytoene synthase (Accessions: EF203260, EC 2.5.1.-), phytoene desaturase (Accessions: DQ369754, EC 1.3.99.-), lycopene beta cyclase (Accessions: EF183522, EC 1.14.-.-), lycopene epsilon cyclase (Accessions: AB205046, EC 1.14.-.-), zeaxanthin glycosyl transferase, beta-carotene hydroxylase (Accessions: EF120636, EC 1.14.13.-), beta-carotene C-4 ketolase (Accessions: X86782, EC 1.13.-.-, 1.14.99.-), multifunctional geranylgeranyl pyrophosphate synthase (Accessions: AY168649), squalene synthase (Accessions: D29016, EC 2.5.1.21), botyrococcene synthase, fatty alcohol forming acyl-CoA reductase (Accessions: AAK80244, EC 1.1.1.*), wax synthase (Accessions: DQ056715, EC 2.3.1.75), alcohol acyltransferase (Accessions: DQ767969, EC 2.3.1.84), β-ketothiolase (acetoacetyl-CoA thiolase; EC 2.3.1.9), acetoacetyl-CoA reductase (EC 1.1.1.36), polyhydroxyalkanoate (PHA) synthase (EC 2.3.1.-, Accessions: AUU28325), phosphotransacetylase (EC 2.3.1.8), poly-beta-hydroxybutyrate (PHB) synthase (Accessions: AB014757, EC 2.3.1.-) and combinations thereof.

In some examples it is additionally useful to increase fatty acid production in the microorganism. Increases in fatty acid production may be accomplished by over expressing a variety of genes. For example the over expression of thioesterase II (EC 3.1.2.14), acetyl-CoA carboxylase (Accessions: XM_001348802, EC 6.4.1.2), acyl-CoA synthase (Accessions: DVU3065, EC 2.3.1.86), PDH (Accessions: BAB34380, AAC73227, AAC73226, EC 1.2.4.1), PanK (also referred to as coaA, Accessions: AAC76952, EC 2.7.1.33), aceEF (Accessions: AAC73227, AAC73226, EC 1.2.4.1, 2.3.1.61), fabH (Accessions: AAC74175, EC 2.3.1.180), fabD (Accessions: AAC74176, EC 2.3.1.39, 2.3.1.85), fabG (Accessions: AAC74177, EC 1.1.1.100), acpP (Accessions: AAC74178, EC 1.6.5.3, 1.6.99.3), fabF (Accessions: AAC74179, EC 2.3.1.179), sfa (Accessions: AAN79592), β-ketothiolase (also referred to as acetoacetyl-CoA thiolase; Accessions: CAI09076, EC 2.3.1.9), acetoacetyl-CoA reductase (Accessions: CAI08797, EC 1.1.1.36), PHA synthase (E.C. 2.3.1.-, Accessions: AUU28325), phosphotransacetylase (Accessions: AAP77906, EC 2.3.1.8), poly-beta-hydroxybutyrate (PHB) synthase (Accessions: AB014757), phaG gene 4086622 from *Psuedomonas entophilia* L48, a 3'-hydroxyl acyl ACP Coenzyme A translacylase, or combinations thereof, can be used to increase fatty acid production.

In yet other examples it is additionally useful to increase fatty acid production by knocking out, disabling, or decreasing the expression of a variety of genes. For example, the microorganism can have one or more of the following genes either knocked out, or the expression levels can be decreased (for example, using promoter manipulation the gene expresses less peptide than it would have under the endogenous promoter), C18 specific thioesterase (Accessions: NP_721775, EC 3.1.2.14), C16 specific thioesterase (Accessions: Q9SQI3, EC 3.1.2.22), C14 specific thioesterase (Accessions: Q39473, EC 3.1.2.14, 3.1.2.19), C12 specific thioesterase (Accessions: AAA34215), FadE (Accessions: AAC73325, EC 1.3.99.3, 1.3.99.-), GspA (Accessions: AAC76632, EC 1.1.1.94), LdhA (Accessions: AAC74462, EC 1.1.1.27, 1.1.1.28), pflb (Accessions: AAC73989, EC 2.3.1.54), adhE (Accessions: AAC74323), PTA (Accessions: AAC75357), poxB (Accessions: AAC73958, EC 1.2.2.2), ackA (Accessions: AAC75356, EC 2.7.2.1), ackB (Accessions: BAB81430, EC 2.7.2.1).

Products that can be made include hydrocarbon products, such as fatty acids, isoprenoids, fatty alcohols (including for example, mono-, di-, and tri-alcohols), fatty acid esters, and combinations thereof, as well as polyhydroxyalkanoates, organic acids, and the like.

The synthetic cellulosome can utilize any cellulosic material degrading enzyme known in the art. For example, the cellulosic material catabolizing peptide sequence can be chosen from xylanases (EC 3.2.1.136, 3.2.1.156, 3.2.1.8, Accessions: BAA33543, CAA31109) and silases (EC 3.2.2.-, 2.7.7.7, Accessions: CQ800975), various endoglucanases (EC 3.2.1.4, Accessions: BAA92430, AAG45162, P04955, AAD39739), cellobiohydrolases (Accessions: AAC06139, AAR87745, EC 3.2.1.91, 3.2.1.150), cellulases (EC 3.2.1.58, 3.2.1.4, Accessions: BAA12070, BAB64431), chitinases (EC 3.2.1.14, 3.2.1.17, 3.2.1.-, 3.2.1.91, 3.2.1.8, Accessions: CAA93150, CAD12659), exoglucanases (EC 3.2.1.91, Accessions: AAA23226), mannanases (EC 3.2.1.4, 3.2.1.-, Accessions: CAB52403), lichenases (EC 3.2.1.73, Accessions: P29716), and pectate lyases (EC 4.2.2.2, Accessions: AAG59609), ligninases (Accessions: AAA56852, EC 1.11.1.14) and combinations thereof.

In yet other examples, the production host is a bacteria and the synthetic cellulosome has a scaffoldin domain, a carbohydrate binding module (CBM), a cohesin domain, and a cellulosic material degrading peptide sequence, and a product-forming peptide such as fatty alcohol forming acyl-CoA reductase (Accessions: AAK80244, EC 1.1.1.*), wax synthase (Accessions: DQ056715, EC 2.3.1.75), and/or alcohol acyltransferase (Accessions: DQ767969, EC 2.3.1.84).

In yet other examples, the production host is a bacteria and the synthetic cellulosome has a scaffoldin domain, a CBM, a cohesin domain, and a cellulosic material degrading peptide sequence, and a product-forming peptide such as a geranylphosphate synthase (EC 2.5.1.1), geranylgeranyl pyrophosphate synthase (Accessions: XM_00127554, EC 2.5.1.-), phytoene synthase (Accessions: EF203260, EC 2.5.1.-), phytoene desaturase (Accessions: DQ369754, EC 1.3.99.-), lycopene beta cyclase (Accessions: EF183522, EC 1.14.-.-), lycopene epsilon cyclase (Accessions: AB205046, EC 1.14.-.-), zeaxanthin glycosyl transferase, beta carotene hydroxylase (Accessions: EF120636, EC 1.14.13.-), beta-carotene C-4 ketolase (Accessions: X86782, EC 1.13.-.-), squalene synthase (Accessions: D29016, EC 2.5.1.21), botyrococcene synthase, and/or multifunctional geranylgeranyl pyrophosphate synthase.

In yet other examples, the production host is a bacteria and the synthetic cellulosome has a scaffoldin domain, a CBM, a cohesin domain, and a cellulosic material degrading peptide sequence, and a product-forming peptide such as β-ketothiolase (acetoacetyl-CoA thiolase; EC 2.3.1.9), acetoacetyl-CoA reductase (EC 1.1.1.36), PHA synthase (E.C. 2.3.1.-, Accessions: AUU28325), phosphotransacetylase (EC 2.3.1.8), and/or poly-beta-hydroxybutyrate (PHB) synthase (Accessions: AB014757).

Methods of producing the products described herein are also provided. These methods include culturing the isolated microorganisms described herein in a fermentation broth including a cellulosic material and collecting the product. In some instances at least 50%, 60%, 70%, 80%, 90%, or 95% of the carbon in the fermentation broth is in the form of cellulosic material. In some embodiments, these methods further include chemical modifications of the product, for example oxidizing, reducing, introducing functional groups, polymerizing, or depolymerizing the product.

Also provided herein are methods of producing squalene, wherein the production host includes exogenous nucleic acid sequences encoding at least one squalene synthase (E.C. 2.5.1.21) as well as exogenous nucleic acid sequences encoding a synthetic cellulosome. The squalene producing microorganism is cultured in a fermentation broth having cellulosic material. The fermentation broth can have for example at least 100 µg/L, 500 µg/L, 1 mg/L, 5 mg/L, 200 mg/L, 700 mg/L, or at least 1 g/L squalene.

Similarly, methods of producing fatty alcohols are provided. These methods include culturing a microorganism expressing a thioesterase gene and a synthetic cellulosome from exogenous nucleic acid sequences, and collecting the fatty alcohol. The fermentation broth can have for example at least 100 µg/L, 500 µg/L, 1 mg/L, 5 mg/L, 200 mg/L, 700 mg/L, or at least 1 g/L fatty alcohol. The carbon chain length can be varied by modulating the activity of endogenous thioesterases, as well as, or in combination with introducing exogenous nucleic acid sequences encoding thioesterases. Therefore, in some embodiments at least 20%, 30%, 40%, 50%, or 60% of the fatty alcohol produced will have carbon chains of from about C2 to about C30. In other embodiments at least 20%, 30%, 40%, 50%, or 60% of the fatty alcohol produced will have carbon chains of from about C8 to about C20.

In some embodiments, these methods further include chemical modifications of the product, for example oxidizing, reducing, introducing functional groups, polymerizing, or depolymerizing the product.

Also provided herein are methods of producing squalene, wherein the production host includes exogenous nucleic acid sequences encoding at least one squalene synthase (E.C. 2.5.1.21) as well as exogenous nucleic acid sequences encoding a synthetic cellulosome. The squalene producing microorganism is cultured in a fermentation broth having cellulosic material. The fermentation broth can have for example at least 100 µg/L, 500 µg/L, 1 mg/L, 5 mg/L, 200 mg/L, 700 mg/L, or at least 1 g/L squalene.

Similarly, methods of producing fatty alcohols are provided. These methods include culturing a microorganism expressing a thioesterase gene and a synthetic cellulosome from exogenous nucleic acid sequences, and collecting the fatty alcohol. The fermentation broth can have for example at least 100 µg/L, 500 µg/L, 1 mg/L, 5 mg/L, 200 mg/L, 700 mg/L, or at least 1 g/L fatty alcohol. The carbon chain length can be varied by modulating the activity of endogenous thioesterases, as well as, or in combination with, introducing exogenous nucleic acid sequences encoding thioesterases. Therefore, in some embodiments at least 20%, 30%, 40%, 50%, or 60% of the fatty alcohol produced will have carbon chains of from about C2 to about C30. In other embodiments at least 20%, 30%, 40%, 50%, or 60% of the fatty alcohol produced will have carbon chains of from about C8 to about C20.

These and other aspects of the disclosure are described in more detail in the accompanying detailed description and examples.

FIGURES

FIG. 1 is a schematic of a complex cellulosome.

SEQUENCE LISTING

SEQ ID NOS: 1-2 show dockerin domain sequences.
SEQ ID NOS: 3-4 show cohesin domain sequences.

DETAILED DESCRIPTION OF THE INVENTION

I. Overview

Recent advancements in technology have enabled the sequencing of whole genomes. The invention thus provides methods and systems that take advantage of the ability to obtain genetic blueprints (e.g., whole genome sequence information) of certain organisms, such as certain microorganisms that have been extensively studied in the past, to re-write or engineer/modify these genetic blueprints. This in turn provides new organisms that have new or improved capabilities, which could not have been achieved via single-gene or single-pathway engineering alone.

The description provides a microorganism that produces hydrocarbons from a renewable resource, such as cellulosic material. "Cellulosic material" as described herein is any material containing cellulose. Cellulosic material also contains additional compounds, including for example, xylan, xylose, hemicellulose, lignin, and other materials commonly found in biomass.

An engineered microorganism that can metabolize cellulosic material expresses peptides that can bind to each other and/or bind to the extracellular surface of the host microorganism and/or bind to the cellulosic material. The engineered microorganism also expresses peptides that convert the cellulosic material into fermentable carbon sources such as, but not limited to, glucose, xylose, arabinose, and other hexoses and pentoses. These fermentable carbon sources are then converted into products via the product-forming peptides expressed in the microorganism. One of ordinary skill in the art will appreciate that the choice of product-forming peptides included in the microorganism will vary depending on which product is being produced. For example, different peptides will be needed to make fatty acids and their derivatives, hydrocarbons, PHAs, isoprenoids, and organic acids. Finally, additional modifications can be made to the microorganism to increase the production of products. Such modifications can include altering the feedback sensitivity of certain enzymes in the product production biosynthetic pathway, decreasing the activity of various by-product pathways and increasing product accumulation outside of the cell.

The synthetic cellulosome encoding genes and the product-forming genes may be from the same heterologous organism with respect to the microbial host. Alternatively, the synthetic cellulosome genes and the product producing genes may be from two or more different heterologous organisms with respect to the microbial host.

A subject composition comprises a subject genetically modified host cell; and, in some embodiments, further comprises one or more further components selected in part, based on the intended use of the genetically modified host cell. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell, and the like.

II. Definitions

As used herein, the term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

As used herein, the term "nucleic acid" refers to polynucleotides such as deoxyribonucleic acid (DNA), and, where appropriate, ribonucleic acid (RNA). The term should also be understood to include, analogs of either RNA or DNA made from nucleotide analogs, and, as applicable to the embodiment being described, single (sense or antisense) and double-stranded polynucleotides.

The term "carbon source" generally refers to a substrate or compound suitable to be used as a source of carbon for bacterial or simple eukaryotic cell growth. Carbon sources may be in various forms, including, but not limited to polymers, carbohydrates such as cellulosic material including cellulooligosaccharides and lignocellulose, acids, alcohols, aldehydes, ketones, amino acids, peptides, etc. These include, for example, various monosaccharides such as glucose, oligosaccharides, polysaccharides, saturated or unsaturated fatty acids, succinate, lactate, acetate, ethanol, etc., or mixtures thereof.

As used herein, the terms "gene" and "recombinant gene" refer to an exogenous nucleic acid sequence which is transcribed and (optionally) translated. Thus, a recombinant gene can comprise an open reading frame encoding a polypeptide. In such instances, the sequence encoding the polypeptide may also be referred to as an "open reading frame". In other embodiments, a gene can simply provide, upon transcription, an antisense transcript, a ribozyme, or other RNA molecule which affects the phenotype of the host cell.

"Transcriptional regulatory sequence" is a generic term used throughout the specification to refer to DNA sequences, such as initiation signals, enhancers, and promoters, which induce or control transcription of a gene or genes with which they are operably linked.

"Operably linked" means that a gene and transcriptional regulatory sequence(s) are connected in such a way as to permit expression of the gene in a manner dependent upon factors interacting with the regulatory sequence(s).

"Exogenous" means a nucleic acid sequence or a peptide sequence that has been inserted into a host cell. An exogenous sequence can result from the cloning of an native gene from a host cell and the reinsertion of that sequence back into the host cell. In most instances, exogenous sequences are sequences that are derived synthetically, or from cells that are distinct from the host cell.

The terms "host cells" and "recombinant host cells" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, a "reporter gene" is a gene whose expression may be assayed; reporter genes may encode any protein that provides a phenotypic marker, for example: a protein that is necessary for cell growth or a toxic protein leading to cell death, e.g., a protein which confers antibiotic resistance or complements an auxotrophic phenotype; a protein detectable by a colorimetric/fluorometric assay leading to the presence or absence of color/fluorescence; or a protein providing a surface antigen for which specific antibodies/ligands are available.

The term "biosynthetic pathway", also referred to as "metabolic pathway", refers to a set of anabolic or catabolic biochemical reactions for converting (transmuting) one chemical species into another. For instance, an antibiotic biosynthetic pathway refers to the set of biochemical reactions which convert primary metabolites to antibiotic intermediates and then to antibiotics. A hydrocarbon biosynthetic pathway refers to the set of biochemical reactions which convert primary metabolites to hydrocarbon intermediates and then to hydrocarbons.

A "hydrocarbon" generally refers to a chemical compound that consists of the elements carbon (C) and hydrogen (H). They all consist of a carbon backbone and atoms of hydrogen attached to that backbone. Sometimes, the term is used as a shortened form of the term "aliphatic hydrocarbon." There are essentially three types of hydrocarbons: (1) aromatic hydrocarbons, which have at least one aromatic ring; (2) saturated hydrocarbons, also known as alkanes, which do not have double, triple or aromatic compounds; (3) unsaturated hydrocarbons, which have one or more double or triple bonds between carbon atoms, and which are divided into: alkenes, alkynes, isoprenoids and dienes.

"Hydrocarbon product" generally refers to a chemical compound that is primarily a hydrocarbon i.e. consists primarily of the elements of carbon and hydrogen, but may also contain one or more atoms other than carbon and hydrogen, including heteroatoms, such as oxygen, nitrogen, or sulfur. These include, but are not limited to fatty alcohols, thiols, esters, waxes, thioesters, ethers, epoxides, acids, and aldehydes, containing two or more carbon atoms, typically from about 2 to about 60 carbon atoms, from about 10 to about 50 carbon atoms, or from about 15 to about 40 atoms, including all stereoisomers.

Biofuel is any fuel that derives from biomass—organisms, such as plants, fermentation waste, or metabolic byproducts, such as manure from cows. It is a renewable energy source, unlike other natural resources such as petroleum, coal and nuclear fuels. Agricultural products specifically grown for use as biofuels and waste from industry, agriculture, forestry, and households—including straw, lumber, manure, sewage, garbage and food leftovers—can be used for the production of bioenergy.

Cellulose $(C_6H_{10}O_5)n$ is a polymer polysaccharide carbohydrate, of beta-glucose. It forms the primary structural component of plants and is not digestible by humans. Cellulose is a common material in plant cell walls and was first noted as such in 1838. Cellulose is the most abundant form of living terrestrial biomass (Crawford, R. L. 1981. Lignin biodegradation and transformation, John Wiley and Sons, New York.). Cellulose is also the major constituent of paper. Cellulose monomers (beta-glucose) are linked together through 1,4 glycosidic bonds.

As used herein, the term "metabolic pathway" includes catabolic pathways and anabolic pathways both natural and engineered i.e. synthetic. Anabolic pathways involve constructing a larger molecule from smaller molecules, a process requiring energy. Catabolic pathways involve breaking down of larger molecules, often releasing energy. An anabolic pathway is referred to herein as "a biosynthetic pathway."

A polynucleotide, polypeptide, or peptides may have a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), Mol. Biol. 215:403-10.

Additionally, the nucleotide sequence of the nucleic acids can be modified for optimal expression to reflect the codon bias of the host cell and a desired secondary structure of the transcript product mRNA. One of ordinary skill in the art will appreciate the likelihood of successful expression if codon usage is biased towards those codons favored by the host and the 5'-terminal of transcript mRNA is readily accessible to the translational machinery of the cell. Determination of preferred codons can be based on a survey of genes derived from the host cell where sequence information is available and mRNA secondary structure can be determined computationally by a variety of known computer programs, such as but not limited to the Vienna package.

Before the present invention is further described, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention pertains. Although any methods and materials similar or equivalent to those described herein can also be used in the practice or testing of the present invention, the preferred methods and materials are now described.

It must be noted that as used herein and in the appended claims, the singular forms "a," "and," and "the" include plural referents unless the context clearly dictates otherwise. Thus, for example, reference to "a biosynthetic intermediate" includes a plurality of such intermediates, reference to "a nucleic acid" includes a plurality of such nucleic acids, and reference to "the genetically modified host cell" includes reference to one or more genetically—modified host cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Other terms and definitions are defined throughout the text as necessary for providing a detailed description.

III. Identification of Heterologous Genes

There are several different ways to obtain heterologous genes responsible for a desired biological activity from a source organism.

A. Sequence Homology

In one approach, if certain enzymes are known to perform certain biological functions, such as carrying out a step of hydrocarbon biosynthesis, or a step of cellulose degradation/digestion, sequence homology search in the target/source microorganism may be performed using these known enzyme sequences as query sequences. This method enables efficient identification of relevant enzymes or biochemical pathways in a target organism, which is known to produce hydrocarbon at high yield (or to efficiently digest a renewable resource such as cellulose), but whose genes responsible for these desirable phenotypes are previously unknown. Sequence homology search is routine in modern biology, while genome sequences of the target organism can now be routinely obtained through whole genome sequencing.

If the genes involved in certain biological process (such as cellulose degradation or hydrocarbon production) are unknown, traditional genetics and biochemical approaches may be used to identify the genes involved. For example, identification of genes involved in biosynthetic pathways is typically carried out by identifying mutant genes that adversely affect the pathway, and isolating the mutant gene.

B. Functional Approach to Obtain Biosynthesis Pathway Genes

Exemplary functional approaches to identify genes/pathways involved in biosynthesis of hydrocarbons are known. These are for illustration, and are by no means limiting. Other functional screening approaches may also be applicable for the same purpose for use in the instant invention.

WO 05/033287 A2 describes a general approach for identifying gene products having activity in a biosynthetic pathway, the teachings of which are incorporated herein by reference.

In general, the methods described therein comprises producing test cells by introducing exogenous nucleic acid encoding candidate gene products into genetically modified host cell, and determining its effect on host cell growth. Specifically, isolated host cells are genetically modified with a nucleotide sequence encoding a biosynthetic pathway enzyme (such as a hydrocarbon biosynthetic pathway enzyme). Synthesis of the enzyme in the host cell (such as by induced expression when the enzyme is under the control of an inducible promoter) results in conversion of a substrate for the enzyme into a biosynthetic pathway intermediate, which intermediate is toxic to the host cell (e.g., growth inhibiting and/or death inducing). When the intermediate is produced in an amount effective to inhibit growth of the genetically modified host cell, any heterologous gene products that can inhibit the accumulation of the toxic intermediate may be potential enzymes involved in the same biosynthetic pathway, by virtue of its ability to use the intermediate.

Whether a genetically modified host cell accumulates a biosynthetic pathway intermediate intracellularly in an amount that is growth inhibiting is readily determined by monitoring the optical density of a liquid culture of the genetically modified host cell, or is readily determined by monitoring the viability of the cells, e.g., by plating the cells on agar containing appropriate growth media at various times during culture of the cells, and counting the number of colonies formed (e.g., colony forming units, cfu).

U.S. Pat. No. 6,261,842 (incorporated herein by reference) provides an alternative approach to identify biosynthetic pathway genes. Specifically, the invention provides methods and compositions for accessing, in a generally unbiased manner, a diverse genetic pool for genes involved in biosynthetic pathways. The method described therein takes a functional approach to screening the genomic libraries, requiring that the expression of the cloned genomic DNA recapitulates a biosynthetic pathway from the source organism, or combines with the gene products of the host organism to form a new chimeric pathway. This can provide a rapid and efficient means for cloning new genes of significant interest and identifying new biosynthetic products produced therefrom.

*Botryococcus braunii* is a photosynthetic microorganism that produces both non isoprenoid based hydrocarbons (alkanes derived from fatty aldehydes) and isoprenoid-based (multiples of C5 isoprene units) hydrocarbons that accumulate intracellularly and are exported to an extracellular matrix. The biosynthetic pathway in this organism, such as those for the production of squalene, botryococcene, and alkanes will be useful for making hydrocarbon products. These hydrocarbons, which would be useful for the production of biofuels and other petroleum derived chemicals, can constitute more than 50% of the cell's mass. Unfortunately, this microorganism is an obligate phototroph that is not easily manipulated by genetic engineering. Thus, cloning the genes involved in this biosynthetic pathway and expressing those genes in a microorganism that can grow in a fermentor and is genetically amenable to the tools of molecular biology will improve the economics of biohydrocarbon production.

Thus in another embodiment, the hydrocarbon-producing genes are obtained from *Botryococcus braunii*.

IV. Expressing in Host Cells

Once the desired genes are identified and cloned from the source organism (e.g., the genes responsible for production of alkanes in *V. furnissii* and the iosprenoid-based hydrocarbons in *B. braunii*, and the genes encoding proteins in the cellulosome), a suitable heterologous host, such as one that is genetically tractable and easily cultivatable, must be chosen for the desired purpose. The heterologous genes can then be introduced into the host microorganism using art-established methods (e.g., bacteria transformation, etc., infra). The genetically modified host cell (such as a prokaryotic cell, like *E. coli*; or a eukaryotic cell, like yeast—*Saccharomyces cerevisiae*, etc.) may be genetically modified with a nucleic acid comprising a nucleotide sequence encoding a biosynthetic pathway enzyme, wherein synthesis of the enzyme in the genetically modified host cell results in conversion of a substrate for the enzyme into the biosynthetic pathway intermediate.

A. Host Cells

The subject host cells (isolated microorganisms or production hosts) are in many embodiments unicellular organisms, or are grown in culture as single cells. In some embodiments, the host cell may be a eukaryotic cell.

Suitable eukaryotic host cells include, but are not limited to, yeast cells, insect cells, plant cells, fungal cells, and algal cells. Suitable eukaryotic host cells include, but are not limited to, *Pichia pastoris, Pichia f nlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorphs, Kluyreromyces* sp., *Kluyreromyces lactis, Candida albicans, Aspergillus nidulans, Aspergillus niger, lspergillus oryzue, Trichoderma reesei, Chrysosporium lucknowense, Fusarium* sp., *Fusarium gramineum, Fusarium venenatum, Neurospora crassa, Chlamydomonas reinhardtii*, or oleaginous yeast, and the like.

In other embodiments, the host cell is a prokaryotic cell. Suitable prokaryotic cells include, but are not limited to, any of a variety of laboratory strains of *E. coli, Lactobacillus* sp., *Salmonella* sp., *Shigella* sp., *Bacillus subtilis, Rhodococcus opacus, Coryneabacterium, Acinetobacter acetoaceticus*, and the like. See, e.g., Carrier et al. (1992) J: Immunol. 148:1176-1181; U.S. Pat. No. 6,447,184; and Sizemore et al. (1995) Science 270:299-302. Examples of *Salmonella* strains which can be employed in the present invention include, but are not limited to, *Salmonella typhi* and *S. enterica*.

Suitable *Shigella* strains include, but are not limited to, *Shigella flexneri, Shigella sonnet*, and *Shigella disenteriae*. Typically, the laboratory strain is one that is non-pathogenic. Non limiting examples of other suitable bacteria include, but are not limited to, *Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like.

For hydrocarbon production using cellulose, a Gram-positive bacterium such as *Bacilus subtilis* may be used, because the cellulosome can be expressed and anchored outside the Gram-positive bacterium.

The identified heterologous genes belonging to one or more biosynthetic pathways may be introduced stably or transiently into a host cell, using established techniques, including, but not limited to, electroporation, calcium phosphate precipitation, DEAE-dextran mediated transfection, liposome-mediated transfection, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like.

In some embodiments, a subject genetically modified host cell comprises one or more nucleic acids that comprise nucleotide sequences encoding one or more biosynthetic pathway enzyme(s), where the nucleic acids are maintained extrachromosomally, e.g., are maintained episomally. For example, in some embodiments, the nucleic acids are plasmids or other expression vectors that do not become integrated into the genome of the genetically modified host cell. In other embodiments, the nucleic acid is integrated into the genome of the genetically modified host cell. Integration includes multiple tandem integrations, multiple non-tandem integrations, targeted integration, and random integration.

Various determining steps may be used to monitor the impact of the expression of exogenous nucleic acid sequences on the host cell. For example, the determining step may be monitoring optical density of a liquid culture comprising the test cell, or identifying a viable test cell. A genetically modified host cell for practicing the method is also provided. The host cell may be genetically modified with a nucleic acid comprising a nucleotide sequence encoding a biosynthetic pathway enzyme, wherein synthesis of the enzyme in the host cell results in conversion of a substrate for the enzyme into a biosynthetic pathway intermediate, which intermediate is produced in an amount effective to inhibit growth of the genetically modified host cell. The host cell may be a prokaryotic cell, or a eukaryotic cell, such as a plant cell.

B. Vectors

Many embodiments of the invention utilizes an expression vector that comprises a nucleotide sequence that encodes a heterologous biosynthetic pathway enzyme. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as *E. coli* and yeast). Thus, for example, a nucleic acid encoding a biosynthetic pathway gene product(s) is included in any one of a variety of expression vectors for expressing the biosynthetic pathway gene product(s). Such vectors include chromosomal, nonchromosomal and synthetic DNA sequences, and may comprise a full or mini transposon for the integration of a desired DNA sequence into the host chromosome. Examples of tranposons include but are not limited to TN5, TN7, and TN10, as well as the engineered transposomes from Epicentre (www.epicentre.com).

Numerous suitable expression vectors are known to those of skill in the art, and many are commercially available. The following vectors are provided by way of example; for bacterial host cells: pQE vectors (Qiagen), pBluescript plasmids, pNH vectors, lambda-ZAP vectors (Stratagene); pTrc99a, pKK223-3, pDR540, and pRIT2T (Pharmacia); for eukaryotic host cells: pXTI, pSGS (Stratagene), pSVK3, pBPV, pMSG, and pSVLSV40 (Pharmacia). However, any other plasmid or other vector, with or without various improvements for expression, may be used so long as it is compatible with the host cell.

Representative examples of vectors which may be used also include viral vectors, phage, plasmids, phagemids, cosmids, phosmids, bacterial artificial chromosomes (BACs), bacteriophage P1, P1-based artificial chromosomes (PACs), yeast artificial chromosomes (YACs), yeast plasmids, and any other vectors suitable for a specific host cell and capable of stably maintaining and expressing a genomic DNA insert of at least 20 kb, and more preferably greater than 50-75 kb.

Standard recombinant DNA techniques can be used to perform in vitro construction of plasmid and viral chromosomes, and transformed such into host cells and clonally propagate them. These cloning systems, whose capacities for exogenous DNA range up to 50 kilobase pairs (kb), are well suited to the analysis and manipulation of small gene clusters from organisms in which the genetic information is tightly packed, as is the case with many microbes. It is increasingly apparent, however, that many of the functional genetic units of interest may span enormous tracts of DNA.

One type of suitable vectors for the present invention are the so-called artificial chromosomes. One feature of these vectors is their ability to carry large genetic inserts, e.g., greater than 50 kb, with enough mitotic and meiotic stabilities to make their genetic manipulation straightforward. P1 and PAC/BAC clones can contain high molecular weight inserts (75-100 kb or 120+ kb); about four to six times larger than Lambda, and two to three times larger than Cosmids. In addition, the low copy number of the P1, PAC or BAC vector, e.g., in a restriction and recombination-deficient *E. coli* host, confer vastly improved stability on these clones. The upper limit on the size of the insert is often great enough that thousands of genes can be included on one vector. Thus, a single vector could provide, through inclusion of gene clusters, all the genes to a specific biosynthetic pathway.

P1-based artificial chromosomes (PACs) and bacterial artificial chromosomes (BACs) have significantly expanded the size of fragments from eukaryotic genomes that can be stably cloned in *E. coli* and the like as plasmid molecules. Advantages of these systems include the low copy number of the vector (based on the single copy F plasmid of *E. coli*), large possible insert size (clones containing inserts of up to 300 Kb have been propagated), stability of clones in vivo, high cloning efficiency, and easy manipulation of clones by standard techniques (Shizuya et al. (1992) *PNAS* 89:8794-8797). The BAC and PAC systems provide a method to construct a stable library of large inserts, which in certain instances can be critical to the success of the subject method. Large inserts may be needed, for example, because a biosynthetic gene cluster(s) of interest may be large, and because large insert size will maximize the total genetic material represented in the library. Biosynthetic genes for secondary metabolites, for example, are in most cases clustered in one region of the chromosome, along with the genes for self-resistance and pathway-specific regulatory genes. Thus, it is probable that entire pathways can be cloned in one large DNA fragment (Vining et al. (1995) Genetics and Biochemistry of Antibiotic Production, Butterworth-Heinemann, Boston), including the genes required to confer resistance on the host. Additionally, secondary metabolites are usually made from simple primary metabolites, such as amino acids, acetate, or common sugars. Many of these building blocks are likely to be present in the *E. coli* cell. Expression of even a tiny fraction of cloned genes will mean success for this project in terms of the discovery of novel compounds.

The utility of the BAC and PAC systems in large-scale genomic mapping efforts has led to the development of protocols optimized specifically for these plasmids with large inserts (Birren et al. (1993) in Pulsed Field Gel Electrophoresis. Academic Press, San Diego; Sheng et al. (1995) *Nucl. Acids Res.* 23:1990-1996; and Wang et al. (1995) *Electrophoresis* 16:1-7), and be readily adapted to construction of BAC and PAC libraries of microbial DNA. Moreover, genes from diverse prokaryotes such as *Thermotoga, Synechocystis, Chromatium, Clostridium, Lactobacillus, Corynebacterium, Bacteroides,* and *Leptospira* can be expressed in *E. coli* either from their own promoters or from promoter-like sequences present within the cloned DNA. See, for example, Black et al. (1995) *J. Bacteriol.* 177:1952; Buysens et al. (1996) *Appl. Environ. Microbial.* 62:865; Chavez et al. (1995) *Plant Mol. Biol.* 28:173; DeLong et al. (1992) *PNAS* 89:5685; and Ding et al. (1993) *J. Gen. Microbiol.* 139:1093; Ferreyra et al. (1993) *J. Bacteria* 175:1514. These species represent seven different phyla of bacteria, and demonstrate that a very wide diversity of heterologous gene expression signals can be utilized in such host cells as *E. coli*. Highly efficient gene expression (including transcriptional, translational, and post-translational processes) will obviously not occur in all cases. There will be unavoidable selections and limitations introduced in the manipulation and expression of genetic material isolated directly from the environment. However, purely on stochastic grounds, the vast microbial diversity in the sampled environment means that many genes will be successfully expressed.

In certain embodiments, the method utilizes cloning vectors that are based on the *E. coli* F-factor replicon. This feature allows for strict copy number control of the clones so that they are stably maintained at 1-2 copies per cell. The stability of the cloned DNA during propagation in an *E. coli* host cell is substantially higher in lower copy number vectors than in multi-copy counterparts (Kim et al, *NAR* 20:1083-1085). The stabilizing effect of BAC and Fosmid vectors is notable especially for certain genomic DNA that are normally unstable in high copy number vectors. This includes genomes of Archaeal origins.

As an exemplary embodiment, the method utilizes the pBeloBAC11 vector. See, for example, Zimmer et al. (1997) *Genomics* 42:217-226; and Cai et al. (1995) *Genomics* 29:413-425. The pBeloBAC11 vector represents the second generation BAC cloning vectors, which was developed from the pBAC108L by introducing the LacZ gene to facilitate recombinant identification with blue and colorless (white) phenotypes. pBeloBAC11 is a mini-F factor based plasmid. There are three unique cloning sites: Bam HI, SphI, and Hind III, which are flanked by the T7 and SP6 promoters. These promoters can facilitate generating RNA probes for chromosome walking and DNA sequencing of the insert fragment at the vector-insert junction. The G+C rich restriction sites (Not I, Eag I, Xma I, Sma I, Bgl I, and Sfi I) can be used to excise the inserts of BAC clones. There are two selective markers for cloning purposes: LacZ gene for recombinant selection and CMR (chloramphenicol) for transformant selection. The F factor codes for genes that are essential to regulate its own replication and controls its copy number in a cell. The regulatory genes include oriS, repE, parA, and parB. The oriS and repE mediate the unidirectional replication of the F factor, and the parA and parB maintain copy number at a level of one or two per cell. BAC libraries are generated by ligating size-selected restriction digested DNA with pBeloBAC11 followed by, for example, electroporation into E. coli. This vector allows lacZ-based positive color selection of the BAC clones that have insert DNA in the cloning sites at the time of library construction.

The construction of BAC libraries using pBeloBAC11 can be carried out by any of number of ways. Merely for illustration, the vector is first digested with HindIII, Bam HI or SphI and then dephosphorylated to prevent self ligation. Next, high molecular weight DNA is partially digested with HindIII, Bam HI or SphI, or linkers containing such sites are added as flanking sequences thereto, and size-selected DNA are ligated into the vector. The vector can then be electroporated into appropriate host cells. Recombinant transformants are selected on media containing chloramphenicol, X-Gal, and IPTG. After recombinant transformants are detected, their size can be assayed by a simple plasmid DNA minipreparation followed by digestion with NotI to free the DNA insert from the vector, and CHEF electrophoresis. The most widely used E. coli strain for BAC cloning is DH10B (Hanahan, (1983) J. Mol. Biol. 166:557-580). Key features of this strain include mutations that block: 1) restriction of foreign DNA by endogenous restriction endonucleases (hsdRMS); 2) restriction of DNA containing methylated DNA (5' methyl cytosine or methyl adenine residues, and 5' hydroxymethyl cytosine) (mcrA, mcrB, mcrC, and mrr); 3) recombination (recA1).

Another family of vectors which can be used in the subject method is the PAC vectors. The PAC vectors have most of the features of the BAC system however the vectors contain the SacB gene which provides a positive selection for recombinant clones during library construction. sacB encodes sucrose synthase. When cells are grown in the presence of saccharose, sucrose synthase will degrade saccharose into levan which is highly toxic to E. coli. The BamHI cloning site is within sacB and thus disruption of sacB by insertion of a large DNA fragment allows for growth of the cell on media containing saccharose. Additionally the vector has a "pUC19-link", containing a high copy number origin of DNA replication, which is used for convenient vector propagation and is later removed during vector preparation for library construction.

Still another suitable BAC vector is the pFOS1 vector, which is a single copy cosmid vector constructed by fusing pBAC108L and pUCcos (a pUC vector in which the region including lacZ and multiple cloning sites was replaced by lambda cos sequence). In vivo homologous recombination between two vectors via cos sites resulted in pFOS1. The vector is extremely unstable in most of E. coli strains due to the presence of double cos sites. pop2136 strain (Methods in Enzymology vol. 152 pp 173-180, 1987), for no apparent reason, can maintain pFOS1 (and other double-cos cosmid vectors) with some stability. The bireplicon is driven by the pUC replication origin, and exists in high copies in E. coli. After in vitro packaging and transfection to E. coli, the structure of Fosmids is exactly the same as pBAC108L clones except the size; therefore Fosmids are mini-BACs with 40 kb inserts. Fosmid library can easily be constructed using the protocol for constructing cosmid libraries with double-cos vectors. The Fosmid system is useful for quickly generating miniBAC libraries from small amounts of source DNA, such as flow-sorted chromosomal DNA.

The subject vectors will generally contain a selectable marker gene. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. As set out above, the pBeloBAC11 vector includes a gene providing chloramphenicol resistance for transformant selection.

In certain instances, it may desirable to express the genomic orfs in a eukaryotic cell, such as a fungal host cell. Functional characterization of genes within a given PAC or BAC clone can be carried out by transferring the DNA into eukaryotic cells for transient or long-term expression. To facilitate transfection studies, the vector can be engineered to include a marker gene which is selectable in the eukaryotic host cell. These retrofitting protocols may be applied with a number of markers of interest to extend the functionality of PAC and BAC libraries, and specialized aspects of such manipulation of E. coli-based artificial chromosomes are outlined in, for example, Mejia et al. (1997) Genome Res 7:179-86.

The vector should include at least one origin of replication for the host cell into which the vector is to be transfected. If also necessary, the vector can include one or more copy-control sequence for controlling the number of copies of the vector in any one cell. By way of illustration, for use in E. coli and other bacterial host cells, the vector preferably includes one or more bacterial origins of replication (Ori), and preferably ones which do not adversely affect gene expression in infected cells. For example, the bacterial On can be a pUC bacterial On relative (e.g., pUC, colEI, pSC101, p15A and the like). The bacterial origin of replication can also, for example, be a RK2 OriV or f1 phage Ori. The vectors also further include a single stranded replication origin, such as an f1 single-stranded replication origin.

The vector is transfected into and propagated in the appropriate host. Methods for transfecting the host cells with the genomic DNA vector can be readily adapted from those procedures which are known in the art. For example, the genomic DNA vector can be introduced into the host cell by such techniques as the use electroporation, precipitation with DEAE-Dextran or calcium phosphate, or lipofection.

The biosynthetic pathway gene product-encoding nucleotide sequence in the expression vector is operably linked to an appropriate expression control sequence(s) (promoter) to direct synthesis of the encoded gene product. Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544).

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), apagC promoter (Pulkkinen and Miller, J: Bacteriol., 1991: 173 (1): 86-93; Alpuche-Aranda et al., *PNAS,* 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfeld et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367-378); a tet promoter (see, e.g., Hillen, W. and Wissmann, A. (1989) In Saenger, W. and Heinemann, U. (eds), *Topics in Molecular and Structural Biology, Protein-Nucleic Acid Interaction.* Macmillan, London, UK, Vol. 10, pp. 143-162); an SP6 promoter (see, e.g., Melton et al. (1984) *Nucl. Acids Res.* 12:7035-7056); and the like.

Non-limiting examples of suitable eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

In addition, the expression vectors will in many embodiments contain one or more selectable marker genes to provide a phenotypic trait for selection of transformed host cells such as dihydrofolate reductase or neomycin resistance for eukaryotic cell culture, or such as tetracycline or ampicillin resistance in prokaryotic host cells such as *E. coli.*

Generally, recombinant expression vectors will include origins of replication and selectable markers permitting transformation of the host cell, e.g., the ampicillin resistance gene of *E. coli,* the *S. cerevisiae* TRP 1 gene, etc.; and a promoter derived from a highly expressed gene to direct transcription of the biosynthetic pathway gene product-encoding sequence. Such promoters can be derived from operons encoding glycolytic enzymes such as 3-phosphoglycerate kinase (PGK), x-factor, acid phosphatase, or heat shock proteins, among others.

In many embodiments, the host cell is genetically modified with a nucleic acid that includes a nucleotide sequence encoding a biosynthetic pathway gene product (hydrocarbon synthesis/secretion or cellulosome proteins, etc.), where the nucleotide sequence encoding a biosynthetic pathway gene product is operably linked to an inducible promoter. Inducible promoters are well known in the art. Suitable inducible promoters include, but are not limited to, the pL of bacteriophage Plac; Ptrp; Ptac (Ptrp-lac hybrid promoter); an isopropyl-beta-D-thiogalactopyranoside (IPTG) inducible promoter, e.g., a lacZ promoter; a tetracycline-inducible promoter; an arabinose inducible promoter, e.g., PBAD (see, e.g., Guzman et al. (1995) *Bacteria* 177:4121-4130); a xylose-inducible promoter, e.g., Pxyl (see, e.g., Kim et al. (1996) *Gene* 181: 71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda PL promoter, a promoter controlled by a heat-sensitive repressor (e.g., CI857-repressed lambda-based expression vectors; see, e.g., Hoffmann et al. (1999) *FEMS Microbiol Lett.* 177(2):327-34); and the like.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast Saecharomyces, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D.C.).

Alternatively, vectors may be used which promote integration of foreign DNA sequences into the yeast chromosome.

In some embodiments, a subject genetically modified host cell is one that is genetically modified with a nucleic acid comprising a nucleotide sequence encoding a single gene product in a biosynthesis pathway. In other embodiments, a subject host cell is genetically modified with a nucleic acid comprising nucleotide sequences encoding two or more gene products in a biosynthesis pathway. For example, the nucleic acid will in some embodiments comprise nucleotide sequences encoding the first and second enzymes in a biosynthetic pathway. In other embodiments, the nucleic acid will comprise nucleotide sequences encoding the first, second, and third enzymes in a biosynthetic pathway. In other embodiments, the nucleic acid will comprise nucleotide sequences encoding the second, third, and fourth enzymes in a biosynthetic pathway. In other embodiments, the nucleic acid will comprise nucleotide sequences encoding the third, fourth, and fifth enzymes in a biosynthetic pathway. In other embodiments, the nucleic acid will comprise nucleotide sequences encoding the fourth, fifth, and sixth enzymes in a biosynthetic pathway. In other embodiments, the nucleic acid will comprise nucleotide sequences encoding the first, third, and fifth enzymes in a biosynthetic pathway.

Where the host cell is genetically modified to express two or more gene products in a biosynthetic pathway, nucleotide sequences encoding the two or more gene products will in some embodiments each be contained on separate expression vectors. Where the host cell is genetically modified to express two or more gene products in a biosynthetic pathway, nucleotide sequences encoding the two or more gene products will in some embodiments be contained in a single expression vector. Where nucleotide sequences encoding the two or more gene products are contained in a single expression vector, in some embodiments, the nucleotide sequences will be operably linked to a common control element (e.g., a promoter), e. g., the common control element controls expression of all of the biosynthetic pathway gene product-encoding nucleotide sequences on the single expression vector.

In some embodiments, a nucleotide sequence encoding a biosynthetic pathway gene product will be operably linked to an inducible promoter. In other embodiments, a nucleotide sequence encoding a biosynthetic pathway gene product will be operably linked to a constitutive promoter. In some embodiments, where two or more biosynthetic pathway gene products are encoded by two or more nucleotide sequences, one of the nucleotide sequences will be operably linked to an inducible promoter, and one or more of the other nucleotide sequences will be operably linked to a constitutive promoter.

The biosynthetic pathway enzymes produced by a genetically modified host cell are in some embodiments produced at a higher level than the level of such enzymes produced by a control cell, e.g., the same cell not genetically modified with one or more nucleic acids encoding a biosynthetic pathway enzyme(s). Thus, e.g., the biosynthetic pathway enzymes produced by a genetically modified host cell will in some embodiments be produced at a level that is at least 25%, at least 50%, at least 75%, at least 2-fold, or at least 5-fold, or more, higher than the level of such enzymes produced by a control cell, e.g., the same cell not genetically modified with one or more nucleic acids encoding a biosynthetic pathway enzyme(s).

C. Fine-Tuning Expressions

As described above, the heterologous genes may be introduced into the host cell as extra-chromosomal genetic materials that can replicate themselves (e.g., plasmids, BAC, PAC, or artificial chromosome), or as genetic material integrated into the host genome. Regardless of whether the heterologous genes are integrated into the host genome, or exist as extra-chromosomal genetic materials, the optimal expression of heterologous genes belonging to a new metabolic pathway can likely benefit from coordinated expression of such genes, tight control over gene expression, and consistent expression in all kinds of host cells. While numerous gene expression tools have been developed for the overproduction of proteins, these tools may not be ideal for pathway redirection as used in the instant invention.

Methods and systems are provided that fine-tune the expression of heterologous genes, which in turn allow reproducible manipulation of metabolism in model microbes, such as *E. coli, Bacillus subtilis*, and *Aspergillus nidulans*. These methods allow balanced expression of the heterologous genes (e.g., those encoding the cellulosome) by techniques such as fine-tuning mRNA stability, the use of inducible promoters of various strengths, etc. See, for example, Keasling et al., New tools for metabolic engineering of *E. coli*. In Metabolic Engineering, S.-Y. Lee and E. T. Papoutsakis, eds. Marcel Dekker, New York, N.Y. (1999); Keasling, Gene-expression tools for the metabolic engineering of bacteria. Trends in *Biotechnology* 17:452-460, 1999; Martin et al., Redesigning cells for production of complex organic molecules. ASM News 68: 336-343, 2002 (all incorporated herein by reference).

The following subsections describe in detail several illustrative aspects of the improved methods for reproducible manipulation of metabolic pathway genes in model microbes.

1. Controlling mRNA Stability in *E. Coli*

The synthesis of a complex product, such as certain hydrocarbons, may necessitate the cloning and expression of many new genes encoding the enzymes of a metabolic pathway. Thus it might be desirable to construct synthetic operons containing the genes to coordinately regulate the genes involved. This is partly because that in natural operons, the genes of an operon are differentially expressed by differential stability of the genes of the polycistronic mRNA. While there is an extensive scientific literature describing the mechanisms of mRNA degradation, there has been little or no work in applying this knowledge to manipulating bioprocesses.

The invention provides expression systems to take advantage of differential mRNA stability. In certain embodiments, novel DNA cassettes that will form hairpins at the 5'-end of the mRNA after transcription is placed at the 5'-end of a gene. This allows the stabilization of a transcript up to 20-fold over a transcript with no hairpin. Thus, if a gene is being expressed at low levels (where translation is not limiting), this stabilization can lead to a corresponding increase in protein synthesis. While not wishing to be bound by any particular theory, the hairpin at the 5'-end of the mRNA may prevent endonucleases from binding to 5'-end and inactivating the transcript.

In another embodiment, mRNA secondary structures and RNase E cleavage sites may be strategically placed to control the expression of multiple genes required for the synthesis of complex products. By changing gene location in the operon or the nature of the secondary structures or RNase E sites, it is possible to differentially regulate the expression of two genes in a dual-gene operon 1000-fold. This technology may also find general application in pharmaceutical protein production from low-copy plasmids or chromosomally encoded genes, where transcription rather than translation limits protein synthesis. See, for example, Carrier and Keasling, Engineering mRNA stability in *E. coli* by the addition of synthetic hairpins using a 5' cassette system. *Biotechnol. Bioeng.* 55: 577-580, 1997; Carrier and Keasling, Controlling messenger RNA stability in bacteria: strategies for engineering gene expression. *Biotechnol. Prog.* 13: 699-708, 1997; Carrier and Keasling, Mechanistic modelling of mRNA decay. *J. Theor. Biol.* 189: 195-209, 1997; Carrier et al., mRNA stability and plasmid copy number effects on gene expression from an inducible promoter system. *Biotechnol. Bioeng.* 59: 666-672, 1998; Carrier and Keasling, A library of synthetic 5' secondary structures to manipulate mRNA stability in *E. coli*. *Biotechnol. Prog.* 15: 58-64, 1999; Smolke et al., Coordinated, differential expression of two genes through directed mRNA cleavage and stabilization by secondary structures. *Appl. Environ. Microbiol.* 66: 5399-5405, 2000; Smolke et al., Effects of transcription induction homogeneity and transcript stability on expression of two genes in a constructed operon. *Appl. Microbiol. Biotechnol.* 57: 689-696, 2001; Smolke and Keasling, Effect of copy number and mRNA processing and stabilization on transcript and protein levels from an engineered dual-gene operon. *Biotechnol. Bioeng.* 78: 412-424, 2002; Smolke and Keasling, Effect of gene location, mRNA secondary structures, and RNase sites on expression of two genes in an engineered operon. *Biotechnol. Bioeng.* 80: 762-776, 2002.

2. Low-Copy Expression Vectors for *E. coli*

Once one has determined the optimal design for the metabolic pathways, it may be important to accurately and quantitatively express those genes. Unfortunately, current vectors available for expressing genes in bacteria are segregationally unstable, have different copy numbers in the cells of a culture, and are unable to replicate large pieces of DNA.

The invention provide a low-copy cloning vector that exhibits precise control of gene copy number and expression, stable segregation (even while overexpressing a gene), and the ability to replicate the large pieces of DNA requisite for metabolic engineering. Besides its importance for metabolic engineering, this plasmid will find general use in continuous culture of genetically engineered organisms where stability of the plasmid is extremely important. See, for example, Kuo and Keasling, A Monte Carlo simulation of plasmid replication during the bacterial division cycle. *Biotechnol. Bioeng.* 52: 633-647, 1996; Jones and Keasling, Construction and characterization of F plasmid-based expression vectors. *Biotechnol. Bioeng.* 59:659-665, 1998; Carrier et al., mRNA stability and plasmid copy number effects on gene expression from an inducible promoter system. *Biotechnol. Bioeng.* 59: 666-672, 1998; Cooper and Keasling, Cycle-specific replication of chromosomal and F-plasmid origins. *FEMS Microbiol. Lett.* 163: 217-222, 1998; Jones et al., Low-copy plasmids can perform as well as or better than high-copy plasmids for metabolic engineering of bacteria. *Met. Eng.* 2: 328-338, 2000.

3. Promoter Control Systems for *E. coli*

Once one has placed a metabolic pathway under control of a promoter on the low-copy plasmid and determined the strength of expression, it is desirable to actually achieve that level of expression. However, the expression of a heterologous gene may be affected by the physiology of the host organism. For genes placed under the control of phosphate-starvation promoters, intracellular stores of phosphate (polyphosphate) can affect expression. Degradation of polyphosphate during phosphate starvation leads to the release of phosphate from the cell and down-regulation of the phosphate-starvation response.

Thus the invention provides a method to eliminate the gene for polyphosphate degradation (ppx), in order to improve the expression of a heterologous gene from the phosphate-starvation promoter. Besides its importance in enabling more accurate control of gene expression in manipulating metabolism, these strains is also useful in pharmaceutical protein production where the phosphate-starvation system is used to induce gene expression. In addition to reproducible promoter control, it is important that the promoter have consistent expression in all cells of the culture. Unfortunately, many of the carbohydrate-inducible promoters, such as the arabinose-inducible promoter PBAD, are subject to all-or-none induction, in which intermediate concentrations of the inducer (arabinose) give rise to subpopulations of cells that are fully induced and uninduced. In metabolic engineering, these culture heterogeneities can lead to heterogeneities in the final product. Our simulation studies of this phenomenon indicated that the all-or-none response could be alleviated, by placing the gene encoding the protein responsible for transporting the inducer into the cell under control of a promoter that was not responsive to the inducer itself.

For example, to construct a host/vector expression system with regulatable promoter control in a homogeneous population of cells, the gene that encodes the arabinose transport system (araE) of *E. coli* was cloned onto an RSF1010-derived plasmid under control of the IPTG inducible Ptac and Ptaclac promoters. This gene encodes the low-affinity, high-capacity arabinose transport protein and is controlled natively by an arabinose-inducible promoter. The effects of the arabinose concentration and arabinose-independent transport control on population homogeneity were investigated in these strains using flow cytometry. Transport-deficient strains harboring the transporter and reporter plasmids were uniformly induced across the population at all inducer concentrations, and the level of gene expression in individual cells varied with arabinose concentration. This demonstrates the importance of a transport gene that is controlled independently of the inducer to achieve regulatable and consistent induction of gene expression in all cells of the culture. See, for example, Wong et al., A mathematical model of the lac operon: inducer exclusion, catabolite repression, and diauxic growth on glucose and lactose. *Biotechnol. Prog.* 13:132-143, 1996; Van Dien and Keasling, Optimization of polyphosphate degradation and phosphate secretion using hybrid metabolic pathways and engineered host strains. *Biotechnol. Bioeng.* 59:754-761, 1998; Van Dien and Keasling, A dynamic model of the *E. coli* phosphate-starvation response. *J. Theor. Biol.* 190: 37-49, 1998; Van Dien and Keasling, Effect of polyphosphate metabolism on the *E. coli* phosphate-starvation response. *Biotechnol. Prog.* 15(4): 587-593, 1999; Carrier and Keasling, Investigating autocatalytic gene expression systems through mechanistic modeling. *J. Theor. Biol.* 201: 25-36, 1999; Khlebnikov et al., Regulatable arabinose-inducible gene expression system with consistent control in all cells of a culture. *J. Bacteriol.* 182: 7029-7034, 2000; Khlebnikov et al., Homogeneous expression of the PBAD promoter in *E. coli* by constitutive expression of the low-affinity high-capacity AraE transporter. *Microbiology* 147: 3241-3247, 2001; Smolke et al., Effects of transcription induction homogeneity and transcript stability on expression of two genes in a constructed operon. *Appl. Microbiol. Biotechnol.* 57: 689-696, 2001; Khlebnikov et al., Modulation of gene expression from the arabinose-inducible araBAD promoter. *J. Ind. Microbiol. Biotechnol.* 29: 34-37, 2002; Khlebnikov and Keasling, Effect of lacY expression on homogeneity of induction from the Ptac and Ptrc promoters by natural and synthetic inducers. *Biotechnol. Prog.* 18: 672-674, 2002.

4. Chromosome Integration Vectors for *Aspergillus nidulans*

Within *A. nidulans* genetics, there exists a need for tools that will allow controlled integration of large DNA fragments independent of traditional homologous recombination. We have developed an enzyme-mediated DNA insertion system for *A. nidulans* and demonstrated that this systems is useful for inserting DNA into engineered target sequences. Our approach has been to exploit the intron and bi-directional selection properties of the *A. nidulans* pyrG gene as a target for insertion of DNA cassettes. pyrG encodes orotidine-5'-monophosphate decarboxylase (OMP decarboxylase); mutations in pyrG cause auxotrophy for uracil and uridine. The prototrophy conferred by pyrG into pyrG-mutants allows selection of cells carrying the marker in transformation experiments. In contrast to pyrG promoting metabolic independence in the absence of uracil and uridine, cells with wild type OMP decarboxylase (pyrG+) demonstrate a lethal sensitivity to 5-fluoro-orotic acid (5-FOA) in the presence of uracil/uridine. The toxicity of 5-FOA in the presence uracil and uridine for wt pyrG provides a useful negative selection when the intent of a transformation experiment is to target the pyrG locus.

5. Effect of Chromosome Location on Promoter Strength

This aspect of the invention provides a means to test the effect of promoter type, gene location on the chromosome, and gene copy number on gene expression in a host cell. According to this aspect of the invention, various expression vectors are designed, constructed, or modified, with several combinations of selection markers, constitutive and inducible promoters, and expressed genes. These various vectors are then tested for a variety of functions, such as transformation efficiency, gene targeting efficacy, dynamic response of inducible promoters, and metabolic burden on the host. The effect of different chromosomal location on identical expression constructs, and the relation of copy number to overall expression levels can then be studied to optimize the expression of heterologous genes.

6. Codon Usage

In some embodiments, the nucleotide sequence encoding a biosynthetic pathway gene product is modified such that the nucleotide sequence reflects the codon preference for the particular host cell. For example, the nucleotide sequence will in some embodiments be modified for yeast codon preference. See, e.g., Bennetzen and Hall (1982) *J: Biol. Chem.* 257(6): 3026-3031. As another non-limiting example, the nucleotide sequence will in other embodiments be modified for *E. coli* codon preference. See, e.g., Gouy and Gautier (1982) *Nucleic Acids Res.* 10(22):7055-7074; Eyre-Walker (1996) *Mol. Biol. Evol.* 13(6):864-872. See also Nakamura et al. (2000) *Nucleic Acids Res.* 28(1):292. As another non-limiting example, the nucleotide sequence will in other embodiments be modified for *B. subtillis* codon preference.

7. Additional Genetic Modifications

In some embodiments, a subject genetically modified host cell is one that is genetically modified to include one or more nucleic acids comprising a nucleotide sequence(s) that encode hydrocarbon biosynthetic pathway gene product(s); and that is further genetically modified to achieve enhanced production of a hydrocarbon biosynthetic pathway product, and/or that is further genetically modified such that an endogenous biosynthetic pathway gene is functionally disabled. The term "functionally disabled," as used herein in the context of an endogenous biosynthetic pathway gene, refers to a genetic modification of a biosynthetic pathway gene, which modification results in production of a gene product encoded by the gene that is produced at below normal levels, and/or is non-functional.

In some embodiments, the endogenous undesirable gene of a genetically modified host cell is deleted. Any method for deleting a gene can be used. One non-limiting example of a method for deleting apta gene is by use of the kRed recombination system. Datsenko and Wanner (2000) *Proc Nat'l Acad Sci USA* 97(12): p. 6640-5.

8. Increasing Intracellular Concentration of a Biosynthetic Pathway Intermediate In some embodiments, the intracellular concentration (e.g., the concentration of the intermediate in the genetically modified host cell) of the biosynthetic pathway intermediate is increased to further boost the yield of the final product. The intracellular concentration of the intermediate can be increased in a number of ways, including, but not limited to, increasing the concentration in the culture medium of a substrate for a biosynthetic pathway; increasing the catalytic activity of an enzyme that is active in the biosynthetic pathway; increasing the intracellular amount of a substrate (e.g., a primary substrate) for an enzyme that is active in the biosynthetic pathway; and the like.

D. Metabolic Optimization

As part of the optimization process, the invention also provides steps to eliminate undesirable side reactions, if any, that may consume carbon and energy but do not produce useful products (e.g., hydrocarbons). These steps may be helpful in that they may help to improve yields of the desired hydrocarbons from cellulose.

A combination of different approaches, including metabolomics (which may be used to identify undesirable products and metabolic intermediates that accumulate inside the cell), metabolic modeling and isotopic labeling (for determining the flux through metabolic reactions contributing to hydrocarbon production), and established genetic techniques (for eliminating or substantially disabling unwanted metabolic reactions) may be used. For example, metabolic modeling provides a means to quantify fluxes through the cell's metabolic pathways and determine the effect of elimination of key metabolic steps. In addition, metabolomics and metabolic modeling enable better understanding of the effect of eliminating key metabolic steps on production of the desired hydrocarbons.

To predict how a particular manipulation of metabolism will affect cellular metabolism and synthesis of the desired product, a theoretical framework was developed to describe the molar fluxes through all of the known metabolic pathways of the cell. Several important aspects of this theoretical framework include: (i) a relatively complete database of known pathways in *E. coli*, (ii) incorporation of the growth-rate dependence of cell composition and energy requirements, (iii) experimental measurements of the amino acid composition of proteins and the fatty acid composition of membranes at different growth rates and dilution rates. These new developments allow accurate prediction of fluxes in key metabolic pathways and regulation of enzyme activity.

These types of models have been applied, for example, to analyze metabolic fluxes in organisms responsible for enhanced biological phosphorus removal in wastewater treatment reactors and in filamentous fungi producing polyketides. See, for example, Pramanik and Keasling, A stoichiometric model of *E. coli* metabolism: incorporation of growth-rate dependent biomass composition and mechanistic energy requirements. *Biotechnol. Bioeng.* 56:398-421, 1997; Pramanik and Keasling, Effect of carbon source and growth rate on biomass composition and metabolic flux predictions of a stoichiometric model. *Biotechnol. Bioeng.* 60:230-238, 1998; Pramanik et al., A flux-based stoichiometric model of enhanced biological phosphorus removal metabolism. *Wat. Sci. Tech.* 37: 609-613, 1998; Pramanik et al., Development and validation of a flux-based stoichiometric model for enhanced biological phosphorus removal metabolism. *Water Research* 33: 462-476, 1998.

V. Making Cellulosic Material Catabolizing Microorganism

Naturally occurring cellulosomes are complexes formed by the association of multiple peptides. These peptides fulfill the functions of: 1) adhering the complex to the cell wall of the host organism which expresses the peptides in the complex; 2) adhering the peptides to each other; and 3) degrading carbon sources in the fermentation environment to simple sugars that can be utilized by the organism. Synthetic cellulosomes are designed to fulfill these functions through the expression of one or more exogenous nucleic acid sequences that encode one or more peptides which in turn can have multiple domains. Synthetic cellulosomes can be as simple as a single peptide with a domain that functions to anchor the peptide to the extracellular membrane and a second domain with cellulosic material catabolizing activity. Synthetic cellulosomes can be also as complex as naturally occurring cellulosomes, except that such synthetic cellulosomes will be derived, as least in part, from the expression of exogenous nucleic acid sequences.

The schematic shown in FIG. 1 depicts a generic cellulosome structure.

As stated above, naturally occurring cellulosomes are generally complexes of many protein sequences. The cellulooligosacharride degrading sequence will contain a dockerin domain containing sequences such as those provided in SEQ ID NOS: 1-2 (also described, Raghothama et. al., *Nature Structural Biology,* 8: 775-778, 2001, and B. Lytle, and J. H. Wu, *J. Bacteriol.,* 180 (24), 6581-6585, 1998). These dockerin domains serve to bind the cellulooligosaccharide degrading sequence to a peptide referred to as a scaffoldin peptide. The scaffoldin peptide can contain sequences such as those show in U. T. Gerngross et. al., Mol. *Microbiology,* 8 (2), 325-334, 1993, and L. J. Shimon et. al., *Structure, Mar* 15; 5(3), 381-390, 1997 (SEQ ID NOS: 3-4) which are described as cohesin domains that bind to the dockerin domains on the enzymatic sequence.

A. Design of Synthetic Cellulosome

The design of a particular synthetic cellulosome will depend on the type of feedstock chosen. Exemplary feedstocks include alfalfa, corn stover, crop residues, debarking waste, forage grasses, forest residues, municipal solid waste, paper mill residue, pomace, scraps & spoilage (fruit & vegetable processing), sawdust, spent grains, spent hops, switchgrass, waste wood chips, wood chips. The molecular form which the digestable carbon is available in varies with the choice of feedstock. Some feedstocks will have the majority of carbon available in cellulose (6 carbon polymers) other feedstocks will have a significant amount of carbon available in hemicellulose (5 carbon and 6 carbon mixed matrix). In some instances the feedstock can be pretreated using heat, acid treatment or base treatment. Therefore, the choice of feedstock degrading peptides used can be optimized depending on the structure of the chosen feedstock and whether a pretreatment is used. Possible pre-treatments include the use of dilute acid, steam explosion, ammonia fiber explosion (AMFE), organic solvents (BioCycle, May 2005 News Bulletin, and see: Ethanol from Cellulose: A General Review, P. Badger, p. 17-21 in J. Janick and A. Whipkey (eds.), Trends in New Crops and Uses, ASHS Press, 2002).

A. Cellulosic Material Catabolizing Peptides

Hemicellulose consists of short, highly branched chains of sugars. In contrast to cellulose, which is a polymer of only glucose, a hemicellulose is a polymer of five different sugars. It contains five-carbon sugars (usually D-xylose and L-arabinose) and six-carbon sugars (D-galactose, D-glucose, and D-mannose) and uronic acid. The sugars are highly substituted with acetic acid. The branched nature of hemicellulose renders it amorphous and relatively easy to hydrolyze to its constituent sugars compared to cellulose. When hydrolyzed, the hemicellulose from hardwoods releases products high in xylose (a five-carbon sugar). The hemicellulose contained in softwoods, by contrast, yields more six-carbon sugars.

Peptides having the ability to convert the hemicellulose components into carbon sources that can be used by the microorganism include for example, xylanase (E.C. 3.2.1.136, 3.2.1.156, 3.2.1.8, Accessions: BAA33543, CAA31109) and silase (E.C. 3.2.2.-, 2.7.7.7, Accessions: CQ800975), various endoglucanases (E.C. 3.2.1.4, Accessions: BAA92430, AAG45162, P04955, AAD39739), cellobiohydrolases (Accessions: AAC06139, AAR87745, EC 3.2.1.91, 3.2.1.150), cellulases (E.C. 3.2.1.58, 3.2.1.4, Accessions: BAA12070, BAB64431), chitinases (E.C. 3.2.1.14, 3.2.1.17, 3.2.1.-, 3.2.1.91, 3.2.1.8, Accessions: CAA93150, CAD12659), exoglucanases (E.C. 3.2.1.91, Accessions: AAA23226), mannanases (E.C. 3.2.1.4, 3.2.1.-, Accessions: CAB52403), lichenases (E.C. 3.2.1.73, Accessions: P29716), and pectate lyases (E.C. 4.2.2.2, Accessions: AAG59609).

Many feedstock will contain lignin as well as cellulose. Lignin is a chemical compound that is an integral part of the cell walls of some cells, e.g., tracheids, xylary fibres and sclereids of plants. Lignin polymers are mostly made of heterogenous and irregular arrangements of phenylpropanoid units linked to each other through different kinds of bonds. Lignin polymers are probably network structures with molecular weights on the order of 10,000 amu. Such polymer resists chemical or enzymatic degradation to protect cellulose.

Lignin degradation by white rot fungi has been extensively studied, and results revealed that a constellation of oxidases, peroxidases, and hydrogen peroxide are responsible for generating highly reactive free radicals that undergo a complex series of spontaneous cleavage reactions. Among them, three kinds of extracellular phenoloxidases, namely, lignin peroxidase (LiP) (Accessions: X54257, EC 1.11.1.14), manganese peroxidase (MnP) (Accessions: DQ249811, DQ249812, EC 1.11.1.13), and laccase (Lac) (Accessions: BAB86450, EC 1.10.3.2), are responsible for initiating the depolymerization of lignin (Kirk and Farrell, Annu. Rev. Microbiol. 41: 465, 1987). The expression pattern of these enzymes depends on the organisms: some secrete LiP and MnP (no Lac), whereas others secrete MnP and Lac (no LiP). These enzymes are also unusually nonspecific. In addition to lignin, white rot fungi are able to degrade a variety of environmentally persistent pollutants, such as chlorinated aromatic compounds, heterocyclic aromatic hydrocarbons, various dyes and synthetic high polymers (Bumpus et al., *Science* 228: 1434, 1985). Probably, this degradability of white rot fungi is due to the strong oxidative activity and the low substrate specificity of their ligninolytic enzymes. Thus, white rot fungi and their enzymes are useful as heterologous genes that can confer a host organism the ability to utilize lignin as renewable energy source for hydrocarbon synthesis. For further review, see Cullen and Kersten, "Enzymology and molecular biology of lignin degradation," in The Mycota III: biochemistry and molecular biology. Berlin; Heidelberg: Springer-Verlag, 2004: Pages 249-273, incorporate herein by reference). This review provides an overview of the physiology and genetics of lignin degradation by white rot basidiomycetes. Recent completion of a draft genome sequence has established *P. chrysosporium* as the premier model system. *P. chrysosporium* strains simultaneously degrade cellulose, hemicellulose and lignin, whereas others such as *Ceriporiopsis subvermispora* tend to remove lignin in advance of cellulose and hemicellulose.

Other enzymes involved in lignin degradation which may also be isolated from *P. chrysosporium* and other white rot fungi include: glyoxal oxidase (GLOX); flavin adenine dinucleotide enzymes such as pyranose 2-oxidase, aryl alcohol oxidase, cellobiose dehydrogenase (CDH); and other auxiliary enzymes such as methanol oxidase (Asada et al., *Kagawa Daigaku Nogakubu Gakujutsu Hokoku* 47: 61-70 1995), 1,4-benzoquinone reductase (Brock et al., *Appl Environ Microbiol* 61: 3076-3081, 1995; Brock and Gold, *Arch Biochem Biophys* 331: 31-40, 1996), methyltransferases (Harper et al., *Appl Environ Microbiol* 56: 3450-3457, 1990; Jeffers et al., *Microbiol Reading* 143: 1975-1981, 1997), a cytochrome P450 (Kullman and Matsumura, *Appl Environ Microbiol* 63: 2741-2746, 1997), L-phenylalanine ammonia-lyase (Hattori et al., *FEMS Microbiol Lett* 179: 305-309, 1999), 1,2,4-trihydroxybenzene 1,2-dioxygenase (Rieble et al., *J Bacteriol* 176: 4838-4844, 1994), glutathione transferases (Dowd et al., *Biochem J* 324: 243-248, 1997), superoxide dismutase (Ozturk et al., *Enzyme Microb Technol* 25: 392-399 1999) and catalase (Kwon and Anderson, *Curr Microbiol* 42: 8-11, 2001).

For expression of these genes in heterologous hosts, techniques are now available for recovery of MnP (Whitwam et al., *Biochem Biophys Res Commun* 216: 1013-1017, 1995; Miyazaki and Takahashi, *FEBS Lett* 509: 111-114, 2001; Reading and Aust, *Biotechnol Prog* 16: 326-407-4111, 2000; Reading and Aust, *Biochemistry* 40: 8161-8168, 2001) and LiP (Doyle and Smith, Biochem J 315 (Ptl): 15-19, 1996; Nie et al., *Biochem Biophys Res Commun* 249: 146-150, 1998; Nie et al., *Arch Biochem Biophys* 365: 328-334, 1999) from inclusion bodies. Baculovirus systems have been used to produce active recombinant MnP isozyme H4 (Pease et al., "Lignin-degrading enzymes from the filamentous fungus *Phanerochaete chrysosporium*." In: Biocatalysts for industry. Dordick J S (ed), Plenum Press, New York, pp. 115-135 1991) and LiP isozymes H2 (Johnson et al., *Arch Biochem Biophys* 296: 660-666, 1992) and H8 (Johnson and Li, *Arch Biochem Biophys* 291: 371-378, 1991). Improvements in yields have been made (Lin et al., *Appl Biochem Biotechnol* 66: 269-279, 1997). In contrast, highly efficient secretion of active *P. chrysosporium* MnP isozyme H4 has been demonstrated in *Aspergillus oryzae* (Stewart et al., *Appl Environ Microbiol* 62: 860-864, 1996). Expression was under the control of the *A. oryzae* TAKA amylase promoter, and like the baculovirus system, addition of hemin to the cultures increased yields substantially (Stewart et al., *Appl Environ Microbial* 62: 860-864, 1996). The secreted MnP is fully active, and the physical and kinetic properties of the recombinant protein were similar to the native protein. Most recently, a *Pichia pastoris* system has been successfully used to produce active MnP (Gu et al., *Biotechnol Prog* 19: 1403-1409, 2003). A "homologous expression" system, in which mnp or lip transcriptional control is placed under the glyceraldehyde-3-phosphate dehydrogenase promoter, temporally separates production of the recombinant protein from other peroxidases (Mayfield et al., *Appl Environ Microbiol* 60: 4303-4309, 1994; Sollewijn Gelpke et al., *Appl Environ Microbiol* 65: 1670-1674, 1999). Homologous expression can also be driven under the control of the promoter of the translational elongation factor (Ma et al., *Curr Genet* 43: 407-414, 2003). The approach has been successfully employed in various biochemical investigations including structure function studies of MnP (Kusters-van Someren et al., *Biochemistry* 34: 10620-10627, 1995; Sollewijn Gelpke et al., *Arch Biochem Biophys* 381: 16-24, 2000) and LiP (Sollewijn Gelpke et al., *Biochemistry* 41: 3498-3506, 2002). A similar system of "homologous expression" has been developed for production of MnP in Pleurotus using a native *P. ostreatus* promoter (Irie et al., *Appl Microbiol Biotechnol* 55: 566-570, 2001). An MnP gene from *D. squalens* (Li et al., *Arch Biochem Biophys* 385: 348-356, 2001) has also been expressed in *P. chrysosporium* under the control of the gpd promoter.

In contrast to peroxidases, the heterologous expression of fungal laccases has been straightforward. The *A. oryzae* TAKA amylase system has been successfully used for the production of *T. villosa, R. solani*, and *Coprinus cinereus* laccases (Wahleithmer et al., *Curr Genet* 29: 395-403, 1995; Yaver et al., *Gene* 181: 95-102, 1996; Yaver et al., *Appl Environ Microbiol* 65: 4943-4948, 1999). *T. versicolor* laccases have been produced using *P. pastoris* (Jonsson et al., *Curr Genet* 32: 425-430, 1997; O'Callaghan et al., *J Ind Microbiol Biotechnol* 29: 55-59, 2002) and *S. cerevisiae* (Cassland and Jonsson, *Appl Microbiol Biotechnol* 52: 393-400 1999) systems. Good yields of a *P. cinnabarinus* laccase were obtained in both *A. niger* (Record et al., *Eur J Biochem* 269: 602-609, 2002) and *P. pastoris* (Otterbein et al., *Eur J Biochem* 267: 1619-1625, 2000). The *P. radiata* laccase was efficiently expressed in *T. reesei* under the control of the *T. reesei* cbh1 promoter (Saloheimo and Niku-Paavola, *Bio/Technology* 9: 987-990, 1991). The *Coriolus* (*Trametes*) *hirsutus* laccase gene was expressed in *S. cerevisiae* (Kojima et al., *J Biol Chem* 256: 15224-15230, 1990).

Glyoxal oxidase is efficiently expressed in *Aspergillus nidulans* under the control of the *A. niger* glucoamylase promoter (Kersten et al., *J Bacteriol* 177: 6106-6110, 1995). Under maltose induction, fully active GLOX was secreted by *A. nidulans* at levels 50-fold greater than optimized *P. chrysosporium* cultures, and subsequent yield improvements were obtained using *P. pastoris* (Whittaker et al., *J Biol Chem* 274: 36226-36232, 1999). Site-specific mutagenesis enabled production of recombinant GLOX isozymes corresponding to the native allelic variants (Kersten et al., *J Bacteriol* 177: 6106-6110, 1995). FAD-dependent enzymes have been successfully expressed in *Aspergillus* (Varela et al., *Biochim Biophys Acta* 1546: 107-113, 2001) as well as the "homologous" *P. chrysosporium* system (Li et al., *Biochem Biophys Res Commun* 270: 141-146, 2000; Rotsaert et al., *Arch Biochem Biophys* 390: 206-214. 2001).

Peptides having cellulase activity are useful for including in synthetic cellulosomes.

Cellulases are a class of enzymes produced chiefly by fungi, bacteria, and protozoans that catalyze the hydrolysis of cellulose. However, there are also cellulases produced by other types of organisms such as plants and animals. Several different kinds of cellulases are known, which differ structurally and mechanistically. The EC number for cellulase enzymes is E.C.3.2.1.4. Assays for testing cellulase activity are well known in the art R. Guignard and P. Pilet, Plant and *Cell Physiology*, 17 (5), 899-908, 1976.

Peptides having xylanase activity are useful for including in synthetic cellulosomes. Xylanases is the name given to a class of enzymes which degrade the linear polysaccharide beta-1,4-xylan into xylose, thus breaking down hemicellulose, which is a major component of the cell wall of plants. The EC number for xylanase enzymes is E.C. 3.2.1.136, 3.2.1.156, 3.2.1.8. Assays for testing xylanase activity are well known in the art M. Bailey et. *J. Biotechnology*, 23 (3), 257-270, 1992.

Peptides having phytase activity are also useful for including in synthetic cellulosomes. Phytases break down phytate (phytic acid) releasing phosphorus and calcium. This activity would reduce the production of unwanted by-products from the process. The EC number for phytases is 3.1.32, 3.1.3.26, 3.1.3.8. Assays for testing phytase activity are well known in the art T. W. Kim and X. G. Lei, *J. Anim. Sci.*, 83, 1062-1067, 2005.

B. Structural Peptides

"Structural peptides" as used herein peptides that function to bind the cellulosic material degrading enzyme(s) to the host cell surface, or bind the cellulosic material degrading enzyme(s) to the cellulosic material carbon source. In some instances the synthetic cellulosome is a single peptide have various domains such as multiple structural peptide domains. For example, a synthetic cellulosome can have a cellulosic material degrading enzyme domain, and one or more structural domains. Depending on the structural peptide domain the synthetic cellulosome will bind to the carbon source and serve to place the cellulosic material degrading enzyme activity in close physical proximity to the carbon source. In other examples the synthetic cellulosome will have peptide sequences that bind the synthetic cellulosome to the host cell surface function to place the cellulosic material degrading enzyme activity in close proximity to the cell surface. One of ordinary skill in the art will appreciate that as used herein structural peptides include peptide domains that have been described in the literature as, respectively, Carbohydrate Binding Module (CBM) peptides, S-Layer Homology (SLH) peptides, and scaffoldin peptides.

1. Cloning and Expression

Exemplary structural peptides that have been described in the literature include: CBM (Accessions: ZP_00510056), SLH module (Accessions: ZP_005100961), Scaffoldin (Accesssions: AY221113).

2. Host Specificity

SLH modules may attach to different bacteria in different ways as described in G. Zhao et. al., *Applied Microbiology and Biotechnology*, 70 (4), 464-469, 2005. Depending on the choice of host cell, the SLH module may be engineered to ensure proper adhesion to the cell wall. In some embodiments the SLH module may attach via Secondary Cell Wall Polymers (SCWP) or via peptidoglycans. Peptidoglycan attachment in *E. coli*, a possible preferred host, has been confirmed (see G. Zhao et. al., *Applied Microbiology and Biotechnology*, 70 (4), 464-469, 2005).

VI. Making Products

The following products can be made using combinations of the various molecular biology techniques and molecules disclosed herein. For example, the products described herein can be made via having exogenous genes that are over expressed, endogenous genes that are knocked out or attenuated, and the vectors, promoters, hosts, genetic engineering techniques etc. that have been described herein can be used in various combinations to make the desired products.

A. Hydrocarbons

1. Isoprenoids

Isoprenoids are a structurally diverse family of natural products. Two isoprenoid biosynthetic pathways exist that synthesize the precursors, isopentenyl pyrophosphate (IPP) and its isomer dimethylallyl pyrophosphate (DMAPP). Eukaryotes other than plants use the mevalonate-dependent (MEV) isoprenoid pathway. Plants use both the MEV pathway and the melavonate-independent pathway, or the deoxyxylulose 5-phosphate (DXP) pathway. Either of these pathways can be cloned into a product microorganism to make isoprenoids and their derivatives.

By definition, isoprenoids are made up of so-called isoprene (C5) units. The number of C-atoms present in the isoprenoids can be divided by five (C5, C10, C15, C20, C25, C30 and C40); although irregular isoprenoids and polyterpenes have been reported. Isoprenoid compounds are also referred to as "terpenes" or "terpenoids." Important members of the isoprenoids include the carotenoids, sesquiterpenoids, diterpenoids, and hemiterpenes. Carotenoids include, e. g., lycopene, B-carotene, and the like, many of which function as antioxidants. Sesquiterpenoids, include, e.g., artemisinin, a compound having anti-malarial activity. Diterpenoids, include, e.g., taxol, a cancer chemotherapeutic agent.

The word "pyrophosphate" is used interchangeably herein with "diphosphate." Thus, e.g., the terms "prenyl diphosphate" and "prenyl pyrophosphate" are interchangeable; the terms "isopentenyl pyrophosphate" and "isopentenyl diphosphate" are interchangeable; the terms farnesyl diphosphate" and farnesyl pyrophosphate" are interchangeable; etc. The term "mevalonate pathway" or "MEV pathway" is used herein to refer to the biosynthetic pathway that converts acetyl-CoA to IPP through a MEV pathway intermediate.

As used herein, the term "prenyl diphosphate" is used interchangeably with "prenyl pyrophosphate," and includes monoprenyl diphosphates having a single prenyl group (e.g., IPP and DMAPP), as well as polyprenyl diphosphates that include 2 or more prenyl groups. Monoprenyl diphosphates include isopentenyl pyrophosphate (IPP) and its isomer dimethylallyl pyrophosphate (DMAPP).

As used herein, the term "terpene synthase" refers to any enzyme that enzymatically modifies IPP, DMAPP, or a polyprenyl pyrophosphate, such that a terpenoid compound is produced. The term "terpene synthase" includes enzymes that catalyze the conversion of a prenyl diphosphate into an isoprenoid.

Nucleotide sequences encoding mevalonate pathway gene products are known in the art, and any known mevalonate pathway gene product-encoding nucleotide sequence can used as query sequences to search for homologous genes in any target/source microorganism for creating genetically modified host cells. The following are non-limiting examples of known nucleotide sequences encoding mevalonate pathway gene products, with GenBank Accession numbers and organism following each mevalonate-pathway enzyme, in parentheses: acetoacetyl-CoA thiolase: (NC_000913 REGION: 2324131 . . . 2325315; *E. coli*), (D49362; *Paracoccus denitrificans*), and (L20428; *Saccharomyces cerevisiae*); HMGS: (NC_001145. complement 19061 . . . 20536; *Saccharomyces cerevisiae*), (X96617; *Saccharomyces cerevisiae*), (X83882; *Arabidopsis thaliana*), (AB037907; *Kitasatospora griseola*), and (BT007302; *Homo sapiens*); HMGR: (NM 206548; *Drosophila melanogaster*), (NM_204485; *Callus Callus*), (AB015627; *Streptomyces* sp. KO 3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734 . . . 118898; *Saccharomyces cerevisiae*)); MK: (L77688; *Arabidopsis thaliana*), and (X55875; *Saccharomyces cerevisiae*); PMK: (AF429385; *Hevea brasiliensis*), (NM_006556; *Homo sapiens*), (NC_001145. complement 712315 . . . 713670; *Saccharomyces cerevisiae*); MPD: (X97557; *Saccharomyces cerevisiae*), (AF290095; *Enterococcus faecium*), and (U49260; *Homo sapiens*); and IDI: (NC_000913, 3031087 . . . 3031635; *E. coli*), and (AF082326; *Haematococcus pluvialis*). All other terpene synthase as disclosed in are hereby incorporated herein by reference.

As used herein, the term "prenyl transferase" is used interchangeably with the terms "isoprenyl diphosphate synthase" and "polyprenyl synthase" (e.g., "GPP synthase," "FPP synthase," "OPP synthase," etc.) to refer to an enzyme that catalyzes the consecutive 1'-4 condensation of isopentenyl diphosphate with allylic primer substrates, resulting in the 1 formation of prenyl diphosphates of various chain lengths.

Endogenous MEV pathway genes that can be functionally disabled include one or more of the genes encoding any of the following MEV gene products: HMGS, HMGR, MK, PMK, MPD, and IDI. An endogenous MEV pathway gene can be functionally disabled in any of a variety of ways, including insertion of a mobile genetic element (e.g., a transposon, etc.); deletion of all or part of the gene, such that the gene product is not made, or is truncated and is enzymatically inactive; mutation of the gene such that the gene product is not made, or is truncated and is enzymatically non-functional; deletion or mutation of one or more control elements that control expression of the gene such that the gene product is not made; and the like.

The term "1-deoxy-D-xylulose 5-diphosphate pathway" or "DXP pathway" is used herein to refer to the pathway that converts glyceraldehyde-3-phosphate and pyruvate to IPP and DMAPP through a DXP pathway intermediate.

The genomic screening can be used to isolate genes in various metabolic pathways or biosynthetic pathways. For example, the biosynthetic pathway is a terpene biosynthetic pathway, and wherein the intermediate may be a prenyl diphosphate. The genetically modified host cell may convert acetyl-CoA into a prenyl diphosphate. The genetically modified host cell may be genetically modified with one or more nucleic acids that comprise nucleotide sequences encoding one or more of acetoacetyl-CoA thiolase, hydroxymethylglutaryl-CoA synthase, hydroxymethylglutaryl-CoA reductase, mevalonate kinase, phosphomevalonate kinase, and mevalonate pyrophosphate decarboxylase. Or, the genetically modified host cell may be genetically modified with one or more nucleic acids that comprise nucleotide sequences encoding one or more of acetoacetyl-CoA thiolase, hydroxymethylglutaryl-CoA synthase, hydroxymethylglutaryl-CoA reductase, mevalonate kinase, phosphomevalonate kinase, mevalonate pyrophosphate decarboxylase, and isopentenyl pyrophosphate isomerase. Or, the genetically modified host cell is genetically modified with one or more nucleic acids that comprise nucleotide sequences encoding acetoacetyl-CoA thiolase, hydroxymethylglutaryl-CoA synthase, hydroxymethylglutaryl-CoA reductase, mevalonate kinase, phosphomevalonate kinase, mevalonate pyrophosphate decarboxylase, isopentenyl pyrophosphate isomerase, and a prenyl transferase.

The genetically modified host cell may convert mevalonate or 1-deoxy-D-xylulose-5-phosphate to a prenyl diphosphate, such as a monoprenyl diphosphate or a polyprenyl diphosphate selected from: geranyl diphosphate, farnesyl diphosphate, geranylgeranyl diphosphate, geranylfarnesyl diphosphate, hexaprenyl diphosphate, heptaprenyl diphosphate, octaprenyl diphosphate, solanesyl diphosphate, and decaprenyl diphosphate.

The genetically modified host cell may convert acetyl-CoA into a prenyl diphosphate. It may also be genetically modified with one or more nucleic acids that comprise nucleotide sequences encoding acetoacetyl-CoA thiolase, hydroxymethylglutaryl-CoA synthase, hydroxymethylglutaryl-CoA reductase, mevalonate kinase, phosphomevalonate kinase, and mevalonate pyrophosphate decarboxylase. One or more of the nucleotide sequences may be operably linked to an inducible promoter or a constitutive promoter.

Genetic modifications that enhance production of an endogenous terpene biosynthetic pathway intermediate include, but are not limited to, genetic modifications that result in a reduced level and/or activity of a phosphotransacetylase in the host cell. The intracellular concentration of a terpene biosynthetic pathway intermediate is enhanced by increasing the intracellular concentration of acetyl-CoA. Some hosts like *E. coli* secretes a significant fraction of intracellular acetyl-CoA in the form of acetate into the medium. Deleting the gene encoding phosphotransacetylase, pta, the first enzyme responsible for transforming acetyl-CoA into acetate, reduces acetate secretion. Genetic modifications that reduce the level and/or activity of phosphotransacetylase in a prokaryotic host cell are particularly useful where the genetically modified host cell is one that is genetically modified with a nucleic acid comprising nucleotide sequences encoding one or more MEV pathway gene products.

In some embodiments, a genetic modification that results in a reduced level of phosphotransacetylase in a prokaryotic host cell is a genetic mutation that functionally disables the prokaryotic host cell's endogenous pta gene encoding the phosphotransacetylase. The pta gene, or any other undesirable endogenous genes, can be functionally disabled in any of a variety of ways, including insertion of a mobile genetic element (e.g., a transposon, etc.); deletion of all or part of the gene, such that the gene product is not made, or is truncated and is non-functional in converting acetyl-CoA to acetate; mutation of the gene such that the gene product is not made, or is truncated and is non-functional (e.g., in converting acetyl-CoA to acetate, etc.); deletion or mutation of one or more control elements that control expression of the gene such that the gene product is not made; and the like.

In some embodiments, a genetically modified host cell is one that is genetically modified to include one or more nucleic acids comprising a nucleotide sequence(s) that encode MEV biosynthetic pathway gene product(s); and that is further genetically modified such that an endogenous DXP biosynthetic pathway gene is functionally disabled. In other embodiments, a subject genetically modified host cell is one that is genetically modified to include one or more nucleic acids comprising a nucleotide sequence(s) that encode DXP biosynthetic pathway gene product(s); and that is further genetically modified such that an endogenous MEV biosynthetic pathway gene is functionally disabled.

In some embodiments, where subject genetically modified host cell is a prokaryotic host cell that is genetically modified with nucleic acid(s) comprising nucleotide sequences encoding one or more MEV pathway gene products, the host cell will be further genetically modified such that one or more endogenous DXP pathway genes is functionally disabled. DXP pathway genes that can be functionally disabled include one or more of the genes encoding any of the following DXP gene products: 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, and 1-hydroxy-2-methyl-2-(h)-butenyl 4-diphosphate synthase. An endogenous DXP pathway gene can be functionally disabled in any of a variety of ways, including insertion of a mobile genetic element (e.g., a transposon, etc.); deletion of all or part of the gene, such that the gene product is not made, or is truncated and is enzymatically inactive; mutation of the gene such that the gene product is not made, or is truncated and is enzymatically non-functional; deletion or mutation of one or more control elements that control expression of the gene such that the gene product is not made; and the like.

In other embodiments, where subject genetically modified host cell is a prokaryotic host cell that is genetically modified with nucleic acid(s) comprising nucleotide sequences encoding one or more DXP pathway gene products, the host cell will be further genetically modified such that one or more endogenous MEV pathway genes is functionally disabled.

A host cell genetically modified with a nucleic acid encoding a terpene biosynthetic pathway enzyme is described in detail in WO 2005/033287 as an example (incorporated herein by reference). Such a host cell may be used to identify terpene biosynthetic pathway genes from a target/source organism such as *Botryococcus braunii*. Such a host cell also serves as a working example that heterologous genes can be introduced into a genetically tractable host cell, such as *E. coli* or *B. subtilis*, to confer the host cell a novel or improved functionality originally found in the source microorganism.

2. Carotenoids

Carotenoids consist of eight isoprenoid units joined in such a manner that the arrangement of isoprenoid units is reversed at the center of the molecule so that the two central methyl groups are in a 1,6-position relationship and the remaining nonterminal methyl groups are in a 1,5-position relationship.

As described in U.S. patent application 20050260699, microorganisms that are suitable for producing carotenoids may or may not naturally produce carotenoids, and include prokaryotic and eukaryotic microorganisms, such as bacteria, yeast, and fungi. In particular, yeast such as *Phaffia rhodozyma* (*Xanthophyllomyces dendrorhous*), *Candida utilis*, and *Saccharomyces cerevisiae*, fungi such as *Neurospora crassa, Phycomyces blakesleeanus, Blakeslea trispora*, and *Aspergillus* sp, Archaeabacteria such as *Halobacterium salinarium*, and Eubacteria including *Pantoea* species (formerly called *Erwinia*) such as *Pantoea stewartii* (e.g., ATCC Accession #8200), flavobacteria species such as *Xanthobacter autotrophicus* and *Flavobacterium multivorum, Zymonomonas mobilis, Rhodobacter* species such as *R. sphaeroides* and *R. capsulatus, E. coli*, and *E. vulneris* can be used. Other examples of bacteria that may be used include bacteria in the genus *Sphingomonas* and Gram negative bacteria in the alpha-subdivision, including, for example, *Paracoccus, Azotobacter, Agrobacterium*, and *Erythrobacter*. Eubacteria, and especially *R. sphaeroides* and *R. capsulatus*, are particularly useful. *R. sphaeroides* and *R. capsulatus* naturally produce certain carotenoids and grows on defined media. Such *Rhodobacter* species also are non-pyrogenic, minimizing health concerns about use in nutritional supplements. In some embodiments, it can be useful to produce carotenoids in plants and algae such as *Zea mays, Brassica napus, Lycoper-* sicon esculentum, Tagetes erecta, Haematococcus pluvialis, Dunaliella salina, Chlorella protothecoides, and Neospongiococcum excentrum.

Nucleic acids of the invention can be expressed in microorganisms so that detectable amounts of carotenoids are produced. As used herein, "detectable" refers to the ability to detect the carotenoid and any esters or glycosides thereof using standard analytical methodology. In general, carotenoids can be extracted with an organic solvent such as acetone or methanol and detected by an absorption scan from 400-500 nm in the same organic solvent. In some cases, it is desirable to back-extract with a second organic solvent, such as hexane. The maximal absorbance of each carotenoid depends on the solvent that it is in. For example, in acetone, the maximal absorbance of lutein is at 451 nm, while maximal absorbance of zeaxanthin is at 454 mn. In hexane, the maximal absorbance of lutein and zeaxanthin is 446 nm and 450 nm, respectively. High performance liquid chromatography coupled to mass spectrometry also can be used to detect carotenoids. Two reverse phase columns that are connected in series can be used with a solvent gradient of water and acetone. The first column can be a C30 specialty column designed for carotenoid separation (e.g., YMC Carotenoid S3m; 2.0.times.150 mm, 3 mm particle size; Waters Corporation, PN CT99S031502WT) followed by a C8 Xterra MS column (e.g., Xterra MS C8; 2.1.times.250 mm, 5 mm particle size; Waters Corporation, PN 186000459).

Detectable amounts of carotenoids include 10 µg/g dry cell weight (dcw) and greater. For example, about 10 to 100,000 µg/g dcw, about 100 to 60,000 µg/g dcw, about 500 to 30,000 µg/g dcw, about 1000 to 20,000 µg/g dcw, about 5,000 to 55,000 µg/g dcw, or about 30,000 µg/g dcw to about 55,000 µg/g dcw. With respect to algae or other plants or organisms that produce a particular carotenoid, such as astaxanthin, .beta.-carotene, lycopene, or zeaxanthin, "detectable amount" of carotenoid is an amount that is detectable over the endogenous level in the microorganism.

Depending on the microorganism and the metabolites present within the microorganism, one or more of the following enzymes may be expressed in the microorganism: geranylgeranyl pyrophosphate synthase, phytoene synthase, phytoene desaturase, lycopene .beta.cyclase, lycopene .epsilon.cyclase, zeaxanthin glycosyl transferase, .beta.-carotene hydroxylase, .beta.-carotene C-4 ketolase, squalene synthase, botryococcene synthase and multifunctional geranylgeranyl pyrophosphate synthase. Suitable nucleic acids encoding these enzymes are available from Genbank (see, Accession No. Y15112 for the sequence of carotenoid biosynthesis genes of Paracoccus marcusii; Genbank Accession No. D58420 for the carotenoid biosynthesis genes of Agrobacterium aurantiacum; Genbank Accession No. M87280 M99707 for the sequence of carotenoid biosynthesis genes of Erwinia herbicola; and Genbank Accession No. U62808 for carotenoid biosynthesis genes of Flavobacterium sp. strain R1534.)

Other useful related exogenous nucleic acid sequences that can be expressed to make products include terpene synthases. Terpene synthases will catalyze the prenyl diphosphates to form the following terpenes: IPP will be modified by a terpene synthase to form a 5-carbon hemiterpene; DMAPP will be modified by a terpene synthase to form a 5-carbon hemiterpene; GPP will be modified by a terpene synthase to form a 10-carbon monoterpene; FPP will be modified by a terpene synthase to form a 15-carbon sesquiterpene; and GGPP will be modified by a terpene synthase to form a 20-carbon diterpene.

B. Fatty Acids and Related Products

The fatty acid biosynthetic pathway can be used to make products such as fatty acids, fatty alcohols and fatty acid esters. Such products are made through the expression of one or more exogenous nucleic acid sequences that are expressed in the same host cell that is expressing the synthetic cellulosome.

For example, fatty acid production may be increased (over the endogenous production level) in a host cell. The fatty acid biosynthetic pathway in the production organism starts with the precursors, acetyl CoA and malonyl CoA. E. coli or other host organisms engineered to overproduce these components serve as the core for subsequent engineered steps to define the specific output product (i.e., fatty acid esters, fatty alcohols, and etc). Several different modifications can be made, either in combination, or individually, to the host strain in order to obtain increased acetyl CoA/malonyl CoA/fatty acid production. For example, to increase acetyl CoA production, a plasmid with PDH, PanK, aceEF, (encoding the E1p dehydrogenase component and the E2p dihydrolipoamide acyltransferase component of the pyruvate and 2-oxoglutarate dehydrogenase complexes), fabH/fabD/fabG/acpP/fabF (encoding FAS), and potentially additional DNA encoding fatty-acyl-coA reductases and aldehyde decarbonylases, all under the control of a constitutive promoter, could be constructed. The accession numbers for these genes are: PDH (BAB34380, AAC73227, AAC73226), PanK (also known as coaA, AAC76952), aceEF (AAC73227, AAC73226), fabH (AAC74175), fabD (AAC74176), fabG (AAC74177), acpP (AAC74178), fabF (AAC74179).

Additionally, FadE, GpsA, LdhA, pflb, adhE, PTA, poxB, ackA, and/or ackB may be knocked out, or their expression levels may be reduced, in the engineered microbe by transformation with conditionally replicative or non replicative plasmids containing null mutations of the corresponding genes or by substituting promoter and or enhancer sequences. The accession numbers for these genes are; FadE (AAC73325), GspA (AAC76632), LdhA (AAC74462), pflb (AAC73989), adhE (AAC74323), PTA (AAC75357), poxB (AAC73958), ackA (AAC75356), and ackB (BAB81430).

The resulting engineered microorganisms may be grown in an environment with limited glycerol (less than 1% w/v in the culture medium). As such, these microorganisms will have increased acetyl CoA production levels. Malonyl CoA overproduction may be effected by engineering the microorganism as described above, with DNA encoding accABCD (acetyl CoA carboxylase (Accession number AAC73296, E.C. 6.4.1.2) included in the plasmid synthesized de novo. Fatty acid overproduction may be achieved by further including DNA encoding lipase (Accessions numbers CAA89087, CAA98876) in the plasmid synthesized de novo.

In addition, the plsB (Accession number AAC77011) D311E mutation may be used to remove limitations on the pool of acyl-CoA.

In addition, thioesterases may be added, which release free fatty acids from fattyacyl-ACP. Potential thioesterases may include E. coli TesA (Accession: AAC73596) gene, or a variety of plant thioesterases (see: Fatty acid synthesis genes: Engineering the production of medium-chain fatty acids, H. M. Davies. et. al., p. 176-181, In J. Janick and J. E. Simons (eds.) New Crops, Wiley, N.Y.). In addition the expression of the phaG gene from Psuedomonas sp. that encodes a 3'-hydroxyl-fatty acyl ACP CoA transthioesterase would be useful for the production fatty acyl CoAs from fatty acyl ACP without the need for an intermediate fatty acid CoA ligase, which requires ATP.

In addition, overexpression of the sfa (suppressor of FabA, Accession number AAN79592) gene has been shown to increase production of fatty acids (see: Increased unsaturated fatty acid production associated with a suppressor of the fabA6(Ts) mutation in *E. coli*, C. Rock et. al., *J. Bacteriology*, 178 (18), 5382-5387, 1996).

For various length precursors, specific other genes may be knocked out or their expression levels may be decreased. For example, the thioesterase C18 (accession number AF503757), which uses C20-ACP may be knocked out and the thioesterase P0ADA1, which uses C16-ACP may be included in the synthesized plasmid, thus resulting in the production of predominantly C18. In another example, thioesterases C16 accession number AF503757 and P0ADA1 may be knocked out and the thioesterase Q39473 (which uses C14-ACP) may be included in the synthesized plasmid. For C14, Q39473, AF503757 and P0ADA1 may be knocked out, and AAA34215 (which uses C12-ACP) may be included in the synthesized plasmid. Acetyl CoA, malonyl CoA, and/or fatty acid overproduction can be verified by using radioactive precursors, HPLC, and GC-MS subsequent to cell lysis.

In some embodiments Acetyl-CoA carboxylase (ACC) or Malonyl-CoA decarboxylase may be overexpressed in order to increase the intracellular concentration thereof by at least 2-fold. In a preferred embodiment, Acetyl-CoA carboxylase (ACC) or Malonyl-CoA decarboxylase may be overexpressed in order to increase the intracellular concentration thereof by at least 5-fold. In a more preferred embodiment, Acetyl-CoA carboxylase (ACC) or Malonyl-CoA decarboxylase may be overexpressed so as to increase the intracellular concentration thereof by at least 10-fold.

C. Polyhydroxyalkanoates

Polyhydroxyalkanoates or PHAs are linear polyesters produced in nature by bacterial fermentation of sugar or lipids. More than 100 different monomers can be combined within this family to give materials with extremely different properties.

They can be either thermoplastic or elastomeric materials, with melting points ranging from 40 to 180° C. The most common type of PHA is PHB (poly-beta-hydroxybutyrate).

To produce PHB from a culture of a micro-organism such as *Alcaligenes eutrophus*, that naturally produce PHB, the culture is placed in a suitable medium and fed appropriate nutrients so that it multiplies rapidly. Once the population has reached a substantial level, the 'diet' is changed to force the micro-organism to create PHB. Harvested amounts of PHB from the organism can be anywhere from 30% to 80% of the organisms dry weight.

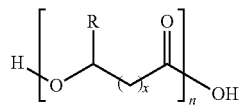

Chain length and side chains can be varied to provide a broad range of physical and mechanical properties. R can be hydrogen or hydrocarbon chains of up to around C13 in length, and x can range from 1 to 3 or more. Varying x and R effect hydrophobicity, Tg, Tm, and level of crystallinity which can range from around 70% to very low, giving excellent stiffness or elasticity as needed.

Genetic engineering has been used to make microorganisms to that produce various PHAs and to produce large quantities of PHAs (see: Engineering *E. Coli* fatty acid metabolism for the production of polyhydroxyalkanoates, Park. et. al., *Enzyme and microbial technology*, 36,579-588, 2005). Any of the enzymes involved in the biosynthesis of PHAs can be expressed from exogenous nucleic acid sequences and used in a production host that is also expressing a synthetic cellulosome. For example, the first reaction consists of a Claisen type condensation of two molecules of acetyl-CoA to form acetoacetyl-CoA. This step is catalyzed by a β-ketothiolase (acetoacetyl-CoA thiolase; EC 2.3.1.9) which when expressed is a product-forming peptide. Acetoacetyl-CoA is then reduced by an acetoacetyl-CoA reductase (EC 1.1.1.36) another product-forming peptide. The activity of acetoacetyl-CoA reductase, produces D-(−)-3-hydroxybutyryl-CoA; this is followed by a polymerization reaction catalyzed by a PHA synthase (E.C. 2.3.1.-, Accessions: AUU28325). Alternatively, enzymes such as phosphotransacetylase (EC 2.3.1.8) can be used to catalyze the conversion of acetyl coenzyme A (acetyl-CoA) to acetyl phosphate, and poly-beta-hydroxybutyrate (PHB) synthase (Accessions: AB014757, EC 2.3.1.-) can then be used to made PHB.

The commercial feasibility of producing PHAs, similar to any fermentation-based product, is in part related to the price of feed stock. Hence, as described herein engineering a microorganism to both produce PHAs, as well as to express synthetic cellulosomes so that that microorganism can degrade cellulosic material carbon sources is beneficial.

EXAMPLES

1. Yeast Engineered to Express Synthetic Cellulosome

Yeast are engineered to express a synthetic cellulosome by preparing a plasmid containing 1 or more cellulosic material-degrading enzymes, a secretion signal, and the alpha-agglutinin domain for cell surface binding and display. This plasmid is amplified in *E. coli* and then transformed into yeast for fermentation, thus producing large quantities of the engineered yeast host.

As a specific, non-limiting example, the method of Y. Fujita et. al., recounted here, is used to express cellulose-degrading enzymes on the yeast cell surface. Plasmids pBG211, for cell surface display of beta-glucosidease from *A. aculeatus* No. F-50 BGL1, and pEG23u31H6 for cell surface display of the EGII gene (egl2, Accessions: AAM41665, EC 3.2.1.4) from *T. reesei* QM9414, are serially transformed in *S. cerevisiae* MT8-1, and propagated on SD medium (6.7 g/L nitrogen base with appropriate supplements such as adenine, leucine, and tryptophan) with 2% glucose as the sole carbon source. To demonstrate the ability of MT8-1/pBGL1/pEG23u31H6 to be able to use celluosic material as a sole carbon source, cells are first grown on SD medium for 48 h at 30° C. The cells are collected by centrifugation, and are resuspended in fresh SD medium with 10-45 g/L of barley beta glucan as the sole carbon source, and the cells are grown aerobically at the same temperature. Cells grown under these conditions produce no detectable glucose as they are degrading the beta glucan and immediately using the glucose for growth.

Other examples of synthetic cellulosomes that have been made include Y. Fujita et. al., *Applied and Environmental Microbiology*, 68 (10), 5136-5141, 2002, and Murai et al., *Applied and Environmental Microbiology*, 64(12):4857-4861, 1998.

2. Yeast Engineered to Express a Hydrocarbon Biosynthetic Gene.

Yeast are engineered to produce amorphadiene by heterologously expressing a gene encoding amorphadiene synthase, ADS (Accessions: DQ448295, EC 4.2.3.24). This enzyme converts farnesyl pyrophosphate produced in the cell to amohphodiene at low but detectable levels. This has been previously reported and described in Dae-Kyun Ro, et al, Nature, 440, 13 Apr., 2006, p 940-943. Plasmid pRS425ADS is constructed as described in Dae-Kyon Ro, et al, and transformed in *Sacharomyces cerevisiae* strain BY4742. Transformants are selected and propagated on SD drop out medium lacking leucine to select for the pRS425ADS plasmid. Transformants grown in the presence of 2% galactose produce detectable amounts of the hydrocarbon product amorphadiene. More amorphadiene can be produced by additional genetic manipulations of the yeast cell as described in Dae-Kyun Ro et al.

3. Yeast Engineered to Express a Synthetic Cellulosome and Hydrocarbon Biosynthetic Gene.

Yeast are engineered to convert cellulosic material to a hydrocarbon product by engineering them to produce both a synthetic cellulosome and hydrocarbon product biosynthetic enzyme. This is achieved by co-expressing the genes encoding the synthetic cellulosome described in example 1 and the gene encoding ADS described in example 2. First the gene encoding ADS is cloned under the control of the GADPH promoter, by replacing the region encoding CMCase translationally fused to the 3' half of alpha agglutinin in plasmid pCMC11 (described in Murai at al, *Appli. Environ. Microbiol.*, 64, 4587-4861, and Muria et al, *Appli. Environ. Microbiol.* 48, 499-503) with the coding sequence for ADS giving plasmid pADS2. Yeast strain MT8-1/pBGL1/pEG23u31H6 is then transformed with plasmid pADS2, and the resulting strain MT8-1/pBGL1/pEG23u31H6/pADS2 are propagated on SD medium lacking histidine, leucine, and uracil. Cells are grown as described in example 1.1 on beta-glucan as the sole carbon source, and they produce detectable amounts of the hydrocarbon product, amorphadiene.

4. Bacteria Engineered to Express Synthetic Cellulosome
*C. acetobutylicum*

Bacteria are engineered to express synthetic cellulosomes by constructing a vector containing a scaffoldin domain, a Carbohydrate Binding Domain (CBM), and one or more cellulosic material-degrading enzymes that have been fused with cohesin domains. One of ordinary skill in the art will appreciate that there are a variety of synthetic cellulosomes that can be made, for example, those described in F. Mingardon et. al., *Applied and Environmental Microbiology*, 71 (3), 1215-1222, 2005, and T. Aria et. al., *PNAS*, 104, 1456-1460, 2007 (which are herein incorporated by reference).

As a specific, but non-limiting example, the method of F. Mingardon et. al, is briefly recounted here. This method can be used to express synthetic cellulosomes containing mannanase enzymes, as well as the other celluosic material degrading enzymes provided herein, in bacteria.

The gene man5K (Accessions: AF316823, EC 3.2.1.-) encoding the mannanase Man5K from *Clostridium cellulolyticum* is cloned as an operon with the gene cipC1 encoding a truncated scaffoldin, miniCipC1 (containing the family 3A CBM, the first X2 domain, the first cohesion domain, and the chimeric miniscaffolidin Scaf3, which contains an additional cohesion domain from CipA of *C. thermocellum* fused at the *C terminus* of miniCipC1 (further described in Perret et al., *J. Bacteriol.* 186:253-257). The expression of the heterologous gene is under the control of a weakened thiolase promoter Pthl. The recombinant strain of the solventogenic bacterium *C. acetobutylicum*, secretes active Man5K in the range of milligrams per liter. The man5K is coexpressed with cipC1 in *C. acetobutylicum* and the recombinant strain secretes full-length mannanase, which binds to the scaffoldin miniCipC1. The secreted heterologous complex is functional. It binds to crystalline cellulose via the carbohydrate binding module of the miniscaffoldin, and the complexed mannanase is active towards galactomannan.

*E. coli.*

Bacteria are engineered to express the synthetic cellulosome by constructing a vector containing a scaffoldin domain, a Carbohydrate Binding Domain (CBM), and one or more cellulosic material-degrading enzymes that have been fused with cohesin domains. As an additionl non limiting example, *E. coli* DH5α is engineered to grow on xylan by expressing a recombinant gene encoding the xylanase 5, xyn5, from *Paenibacillus* sp. strain W-61, as previously described in Ito et al, *Appl. Environ. Microbiol.*, 69, 6969-6978. Plasmid pUX5-S22, a pUC119 derivative carrying the xyn5 gene is transformed into *E. coli* DH5α and stable transformants are isolated and propagated on Luria-Burtani medium containing ampicillin (100 ug/L). To demonstrate growth on xylan, DH5α/pUX5-S22 is grown overnight in the same medium (200 mL) at 37° C. The cells are collected by centrifugation, and the cell pellet is resuspended in 400 mL of M9 medium (pH 7.0) containing 2% (w/v) oat spelt xylan ((Nacalai Tesque), and incubated shaking at 37° C. for 48 hours. The slow release of xylan oligo sacharides and xylose support the detectable growth of the engineered *E. coli.*

5. Bacteria Engineered to Make Hydrocarbon Product(s) from Cellulose Based Feedstock The bacteria engineered to express synthetic cellulosomes described in Example 4, can be further modified to express exogenous nucleic acid sequences that allow for the production of hydrocarbons, such as carotenoids. *E. coli* DH5α/pUX5-S22 (example 2, Ito et al, 2003), are transformed with plasmid pCAR, which is constructed from pTLYC-m4 (described in Sang Hwal Yoon, et al, Appl. Microbiol. Biotechnol. (2007) 74:131-139) by replacing the beta-lactamase with the tetracycline resistance gene from pBR322. pCAR carries the genes encoding crtE, crtB, and crtI and *P. ananatis*, and idi from *E. coli* cloned into the pTrc99A cloning vector, carrying the tetracyline resistance gene in place of the beta-lactamase gene. *E. coli* DH5α/pUX5-S22/pCAR are selected on LB medium containing ampicillin (100 ug/mL) and tetracycline (15 ug/mL). To produce carotenoids from cellulosic material, such as xylan, *E. coli* DH5α/pUX5-S22/pCAR is grown overnight at 37° C. in LB medium containing ampicillin and tetracycline. The resulting cells are harvested by centrifugation and resuspended in minimal medium (400 mL) containing oat spelt xylan (2% w/v), ampicillin and tetracycline, and shaken for 48 h at 37° C. The increase in cell density along with the new production of carotenoids can be observed, demonstrating that the engineered organism can convert the cellulosic material to hydrocarbon product.

6. Bacteria Engineered to Make Fatty Alcohols from Cellulose Based Feedstock

The bacteria engineered to express synthetic cellulosomes described in Example 4, can be further modified to express exogenous nucleic acid sequences that allow for the production of fatty alcohols. For example, the bacteria described in Example 4 can be additionally modified to include the nucleic acid sequences described in this, Example 6, and the bacteria produced will be able to make fatty alcohols from cellulosic materials.

Synthesis of fatty alcohol is achieved by integrating the exogenous nucleic acid sequence for a fatty-alcohol-producing bi-functional acyl-coenzyme A reductase (Accessions: AAD38040) from the jojoba plant into a desired host strain (see: Neutral lipid biosynthesis in engineered *Escherichia coli*: Jojoba oil-like wax esters and fatty butyl esters, R. Kalscheuer et. al., *Applied and Environmental Microbiology*, 72 (2), 1373-1379, 2006).

A specific, but non-limiting example, is to clone into an *E. coli* a vector, such as pACYCDuet-1, pRSFDuet-1, or pCOLADuet-1 (Novagen, Inc., Madison, Wis.) jojoba acyl-coA reductase gene (see: Purification of a jojoba embryo fatty acyl-coenzyme A reductase and expression of its cDNA in high erucic acid rapeseed, J. Metz et. al., *Plant Physiol.*, 122, 635-644, 2000). One of the resulting vectors, such a pACYCDuet 1-JFAR, is transformed into *E. coli* DH5α/pUX5-S22, to give strain *E. coli* DH5α/pUX5-S22/pACYCDuet 1-JFAR, which is selected on LB medium containing ampilcillin and chloramphenicol. Fatty alcohols are produced from cellulosic material by preparing cells as in example 2, except including chloramphenicol in both the LB overnight culture and the minimal (M9) medium 48 hour culture. The observation of cell growth can be monitored by OD 600, and the production of fatty alcohol is monitored by GC/MS analysis of the methanol/Ethyl acetate extracts of the resulting cell pellets.

Those skilled in the art will recognize, or be able to ascertain using no more than routine experimentation, numerous equivalents to the specific method and reagents described herein, including alternatives, variants, additions, deletions, modifications and substitutions. Such equivalents are considered to be within the scope of this invention and are covered by the following claims.

What is claimed is:

1. A method of producing a fatty alcohol product comprising:
   (a) transforming an isolated microorganism with one or more exogenous nucleic acid sequences, wherein the nucleic acid sequences encode (i) a fatty alcohol forming acyl-CoA reductase (EC 1.1.1.*) and (ii) a synthetic cellulosome comprising a xylanase (E.C. 3.2.1.136, 3.2.1.156, 3.2.1.8),
   (b) culturing an isolated microorganism in a fermentation broth comprising a cellulosic material carbon source, wherein the microorganism produces the fatty alcohol product; and
   (c) collecting the fatty alcohol product.

2. The method of claim 1, wherein at least 50% of the carbon source in the fermentation broth is in the form of cellulosic material.

3. The method of claim 1, wherein at least 80% of the carbon source in the fermentation broth is in the form of cellulosic material.

4. The method of claim 1, further comprising substantially rupturing the isolated microorganisms in the fermentation broth prior to collecting the fatty alcohol product.

5. The method of claim 1, further comprising chemically modifying the fatty alcohol product.

6. The method of claim 1, wherein the isolated microorganism is a bacteria.

7. The method of claim 1, wherein the fermentation broth comprises at least 100 µg/L of fatty alcohol.

8. The method of claim 1, wherein at least 20% of the fatty alcohol produced comprises carbon chains of from about C8 to about C20.

* * * * *

UNITED STATES PATENT AND TRADEMARK OFFICE
CERTIFICATE OF CORRECTION

PATENT NO. : 8,535,916 B2  
APPLICATION NO. : 12/526209  
DATED : September 17, 2013  
INVENTOR(S) : Stephen B. Del Cardayre, Shane Brubaker and Jay D. Keasling Page 1 of 1

It is certified that error appears in the above-identified patent and that said Letters Patent is hereby corrected as shown below:

TITLE PAGE
Insert item [60] Related U.S. Application Data below item [22] in order to reflect the Provisional Application data.
Below item [60] Related U.S. Application Data, please insert the following:

--This application is a 371 of PCT/US2007/003736 filed February 13, 2007, which claims benefit of provisional application No. 60/772,682 filed February 13, 2006.--

Signed and Sealed this
Twenty-fourth Day of March, 2015

Michelle K. Lee
*Director of the United States Patent and Trademark Office*